(12) United States Patent
Lee-Sepsick

(10) Patent No.: US 9,238,127 B2
(45) Date of Patent: *Jan. 19, 2016

(54) METHODS AND DEVICES FOR DELIVERING TO CONDUIT

(71) Applicant: Femasys Inc., Suwanee, GA (US)

(72) Inventor: Kathy Lee-Sepsick, Suwanee, GA (US)

(73) Assignee: FEMASYS INC., Suwanee, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/032,162

(22) Filed: Sep. 19, 2013

(65) Prior Publication Data

US 2014/0024934 A1    Jan. 23, 2014

Related U.S. Application Data

(60) Continuation-in-part of application No. 13/684,549, filed on Nov. 25, 2012, which is a continuation of application No. 13/286,127, filed on Oct. 31, 2011, now Pat. No. 8,324,193, which is a division of application No. 12/240,791, filed on Sep. 29, 2008, now Pat. No. 8,052,669, which is a continuation-in-part of application No. 11/065,886, filed on Feb. 24, 2005, now Pat. No. 8,048,086, application No. 14/032,162, which is a continuation-in-part of application No. 13/684,546, filed on Nov. 25, 2012, now Pat. No. 8,726,906, which is a continuation of application No. 13/285,908, filed on Oct. 31, 2011, now Pat. No. 8,336,552, which is a continuation of application No. 12/240,738, filed on Sep. 29, 2008, now Pat. No. 8,048,101, which is a continuation-in-part of application No. 11/065,886, application No. 14/032,162, which is a continuation-in-part of application No. 13/684,529, filed on Nov. 24, 2012, which is a continuation of application No. 13/285,744, filed on Oct. 31, 2011, now Pat. No. 8,316,854, which is a continuation of application No. 11/065,886, application No. 14/032,162, which is a continuation-in-part of application No. 13/684,524, filed on Nov. 24, 2012, now Pat. No. 8,695,606, which is a continuation of application No. 12/504,912, filed on Jul. 17, 2009, now Pat. No. 8,316,853, which is a division of application No. 11/065,886.

(60) Provisional application No. 61/703,002, filed on Sep. 19, 2012, provisional application No. 60/547,491, filed on Feb. 25, 2004, provisional application No. 60/587,604, filed on Jul. 13, 2004.

(51) Int. Cl.

| A61M 31/00 | (2006.01) |
|---|---|
| A61B 17/43 | (2006.01) |
| A61B 17/12 | (2006.01) |
| A61B 17/42 | (2006.01) |
| A61F 6/22 | (2006.01) |
| A61B 17/22 | (2006.01) |
| A61B 17/3207 | (2006.01) |
| A61M 25/06 | (2006.01) |

(52) U.S. Cl.
CPC .......... *A61M 31/00* (2013.01); *A61B 17/12099* (2013.01); *A61B 17/42* (2013.01); *A61B 17/43* (2013.01); *A61F 6/225* (2013.01); *A61B 17/1204* (2013.01); *A61B 17/12136* (2013.01); *A61B 17/22012* (2013.01); *A61B 17/320758* (2013.01); *A61B 2017/22051* (2013.01); *A61B 2017/22084* (2013.01); *A61B 2017/4225* (2013.01); *A61B 2017/4233* (2013.01); *A61M 31/005* (2013.01); *A61M 2025/0681* (2013.01)

(58) Field of Classification Search
None
See application file for complete search history.

(56) References Cited

U.S. PATENT DOCUMENTS

| 1,892,803 | A | 1/1933 | Lawshe |
|---|---|---|---|
| 3,042,030 | A | 7/1962 | Read |
| 3,182,662 | A | 5/1965 | Shirodkar |
| 3,404,682 | A | 10/1968 | Waldron |
| 3,405,711 | A | 10/1968 | Bakunin |
| 3,422,813 | A | 1/1969 | Braley et al. |
| 3,463,141 | A | 8/1969 | Mozolf |
| 3,467,090 | A | 9/1969 | Zollett |
| 3,598,115 | A | 8/1971 | Home |
| 3,645,258 | A | 2/1972 | Massouras |
| 3,675,642 | A | 7/1972 | Lord |
| 3,680,542 | A | 8/1972 | Cimber |
| 3,687,129 | A | 8/1972 | Nuwayser |
| 3,768,102 | A | 10/1973 | Kwan-Gett et al. |
| 3,774,600 | A | 11/1973 | Cognat |

(Continued)

FOREIGN PATENT DOCUMENTS

| CA | 2556747 | 7/2013 |
|---|---|---|
| CN | 200580006068.X | 4/2011 |

(Continued)

OTHER PUBLICATIONS

Frydman, Human Reproduction, 15, 3, 2000.*

(Continued)

*Primary Examiner* — Susan Tran
*Assistant Examiner* — William Craigo
(74) *Attorney, Agent, or Firm* — Ballard Spahr LLP

(57) ABSTRACT

The present invention comprises systems, methods and devices for the delivery of compositions for diagnosing or treating conduits. The delivery system is positioned to allow for placement of the composition into the body conduit. Use of delivery systems, methods and devices for delivering to a body conduit are also included.

14 Claims, 5 Drawing Sheets

(56) References Cited

U.S. PATENT DOCUMENTS

| | | | |
|---|---|---|---|
| 3,803,308 A | 4/1974 | Zipper | |
| 3,805,767 A | 4/1974 | Erb | |
| 3,822,702 A | 7/1974 | Bolduc et al. | |
| 3,855,996 A | 12/1974 | Bolduc | |
| 3,856,016 A | 12/1974 | Davis | |
| 3,858,571 A | 1/1975 | Rudolph | |
| 3,858,586 A | 1/1975 | Lessen | |
| 3,871,374 A | 3/1975 | Bolduc et al. | |
| 3,875,939 A | 4/1975 | Bolduc et al. | |
| 3,882,854 A | 5/1975 | Hulka et al. | |
| 3,918,431 A | 11/1975 | Sinnreich | |
| 3,948,259 A * | 4/1976 | Bolduc et al. | 128/831 |
| 3,954,108 A | 5/1976 | Davis | |
| 3,967,625 A | 7/1976 | Yoon | |
| 3,972,331 A | 8/1976 | Bolduc et al. | |
| 3,973,560 A | 8/1976 | Emmett | |
| RE29,207 E | 5/1977 | Bolduc et al. | |
| RE29,345 E | 8/1977 | Erb | |
| 4,109,654 A | 8/1978 | Bolduc et al. | |
| 4,119,098 A | 10/1978 | Bolduc et al. | |
| 4,126,134 A | 11/1978 | Bolduc et al. | |
| 4,135,495 A | 1/1979 | Borgen | |
| 4,136,695 A | 1/1979 | Dafoe | |
| 4,158,050 A | 6/1979 | Zipper | |
| 4,160,446 A | 7/1979 | Barrington | |
| 4,181,725 A | 1/1980 | Voorhees et al. | |
| 4,182,328 A | 1/1980 | Bolduc et al. | |
| 4,185,618 A | 1/1980 | Corey | |
| 4,207,891 A | 6/1980 | Bolduc | |
| 4,226,239 A | 10/1980 | Polk et al. | |
| 4,230,116 A | 10/1980 | Watson | |
| 4,245,623 A | 1/1981 | Erb | |
| 4,267,839 A | 5/1981 | Laufe et al. | |
| 4,359,454 A | 11/1982 | Hoffman | |
| 4,365,621 A | 12/1982 | Brundin | |
| 4,374,523 A | 2/1983 | Yoon | |
| 4,380,238 A | 4/1983 | Colucci et al. | |
| 4,416,660 A | 11/1983 | Dafoe | |
| 4,466,442 A | 8/1984 | Hilmann et al. | |
| 4,485,814 A | 12/1984 | Yoon | |
| 4,489,725 A | 12/1984 | Casey et al. | |
| 4,509,504 A | 4/1985 | Brundin | |
| 4,523,590 A | 6/1985 | Roth et al. | |
| 4,537,186 A | 8/1985 | Verschoof et al. | |
| 4,547,188 A | 10/1985 | Bolduc | |
| 4,548,201 A | 10/1985 | Yoon | |
| 4,579,110 A | 4/1986 | Hamou | |
| 4,595,000 A | 6/1986 | Hamou | |
| 4,601,698 A | 7/1986 | Moulding, Jr. | |
| 4,606,336 A | 8/1986 | Zeluff | |
| 4,611,602 A | 9/1986 | Bolduc | |
| 4,631,188 A | 12/1986 | Stoy et al. | |
| 4,637,818 A | 1/1987 | Johnson et al. | |
| 4,664,112 A | 5/1987 | Kensey et al. | |
| 4,679,558 A | 7/1987 | Kensey et al. | |
| 4,681,106 A | 7/1987 | Kensey et al. | |
| 4,700,701 A | 10/1987 | Montaldi | |
| 4,700,705 A | 10/1987 | Kensey et al. | |
| 4,713,235 A | 12/1987 | Krall | |
| 4,731,052 A | 3/1988 | Seitz, Jr. | |
| 4,788,966 A | 12/1988 | Yoon | |
| 4,794,927 A | 1/1989 | Yoon | |
| 4,795,438 A | 1/1989 | Kensey et al. | |
| 4,804,691 A | 2/1989 | English et al. | |
| 4,808,399 A | 2/1989 | Rypacek et al. | |
| 4,824,434 A | 4/1989 | Seitz, Jr. | |
| 4,832,941 A | 5/1989 | Berwing et al. | |
| 4,834,091 A | 5/1989 | Ott | |
| 4,847,065 A | 7/1989 | Akimova et al. | |
| 4,869,268 A | 9/1989 | Yoon | |
| 4,932,422 A | 6/1990 | Ragheb | |
| 4,937,254 A | 6/1990 | Sheffield et al. | |
| 4,938,763 A | 7/1990 | Dunn et al. | |
| 4,983,177 A | 1/1991 | Wolf | |
| 5,026,379 A | 6/1991 | Yoon | |
| 5,065,751 A | 11/1991 | Wolf | |
| 5,095,917 A | 3/1992 | Vancaillie | |
| 5,147,353 A | 9/1992 | Everett | |
| 5,193,554 A | 3/1993 | McQuilkin | |
| 5,211,627 A | 5/1993 | William | |
| 5,217,030 A | 6/1993 | Yoon | |
| 5,217,473 A | 6/1993 | Yoon | |
| 5,226,908 A | 7/1993 | Yoon | |
| 5,273,527 A | 12/1993 | Schatz et al. | |
| 5,278,201 A | 1/1994 | Dunn et al. | |
| 5,278,202 A | 1/1994 | Dunn et al. | |
| 5,324,519 A | 6/1994 | Dunn et al. | |
| 5,328,687 A | 7/1994 | Leung et al. | |
| 5,334,209 A | 8/1994 | Yoon | |
| 5,340,849 A | 8/1994 | Dunn et al. | |
| 5,350,798 A | 9/1994 | Linden et al. | |
| 5,352,436 A | 10/1994 | Wheatley et al. | |
| 5,364,345 A | 11/1994 | Lowery et al. | |
| 5,372,584 A * | 12/1994 | Zink et al. | 604/515 |
| 5,374,247 A | 12/1994 | Lowery et al. | |
| 5,389,089 A | 2/1995 | Bauer et al. | |
| 5,391,146 A | 2/1995 | That et al. | |
| 5,464,395 A | 11/1995 | Faxon et al. | |
| 5,469,867 A | 11/1995 | Schmitt | |
| 5,474,089 A | 12/1995 | Waynant | |
| 5,478,837 A | 12/1995 | Rodgers et al. | |
| 5,487,390 A | 1/1996 | Cohen et al. | |
| 5,487,897 A | 1/1996 | Poison et al. | |
| 5,551,443 A | 9/1996 | Sepetka et al. | |
| 5,562,099 A | 10/1996 | Cohen et al. | |
| 5,575,802 A | 11/1996 | McQuilkin et al. | |
| 5,599,552 A | 2/1997 | Dunn et al. | |
| 5,601,600 A | 2/1997 | Ton | |
| 5,612,052 A | 3/1997 | Shalaby | |
| 5,632,727 A | 5/1997 | Tipton et al. | |
| 5,632,753 A | 5/1997 | Loeser | |
| 5,634,877 A | 6/1997 | Salama | |
| 5,681,873 A | 10/1997 | Norton et al. | |
| 5,701,899 A | 12/1997 | Porter | |
| 5,702,716 A | 12/1997 | Dunn et al. | |
| 5,702,717 A | 12/1997 | Cha et al. | |
| 5,704,899 A | 1/1998 | Milo | |
| 5,714,159 A | 2/1998 | Shalaby | |
| 5,716,321 A | 2/1998 | Kerin et al. | |
| 5,725,777 A | 3/1998 | Taylor | |
| 5,733,950 A | 3/1998 | Dunn et al. | |
| 5,736,152 A | 4/1998 | Dunn | |
| 5,739,176 A | 4/1998 | Dunn et al. | |
| 5,744,153 A | 4/1998 | Yewey et al. | |
| 5,746,769 A | 5/1998 | Ton et al. | |
| 5,747,058 A | 5/1998 | Tipton et al. | |
| 5,752,974 A | 5/1998 | Rhee et al. | |
| 5,759,563 A | 6/1998 | Yewey et al. | |
| 5,780,044 A | 7/1998 | Yewey et al. | |
| 5,788,716 A | 8/1998 | Kobren et al. | |
| 5,792,469 A | 8/1998 | Tipton et al. | |
| 5,795,288 A | 8/1998 | Cohen et al. | |
| 5,795,331 A | 8/1998 | Cragg et al. | |
| 5,807,239 A | 9/1998 | DiBernardo | |
| 5,826,584 A | 10/1998 | Schmitt | |
| 5,830,228 A | 11/1998 | Knapp et al. | |
| 5,843,121 A | 12/1998 | Yoon | |
| 5,846,255 A | 12/1998 | Casey | |
| 5,866,554 A | 2/1999 | Shalaby et al. | |
| 5,873,815 A | 2/1999 | Kerin et al. | |
| 5,885,601 A | 3/1999 | Sokal | |
| 5,888,533 A | 3/1999 | Dunn | |
| 5,891,192 A | 4/1999 | Murayama et al. | |
| 5,891,457 A | 4/1999 | Neuwirth | |
| 5,894,022 A | 4/1999 | Ji et al. | |
| 5,919,434 A | 7/1999 | Dugstad et al. | |
| 5,935,056 A | 8/1999 | Kerin et al. | |
| 5,935,098 A | 8/1999 | Blaisdell et al. | |
| 5,935,137 A | 8/1999 | Saadat et al. | |
| 5,947,958 A | 9/1999 | Woodard et al. | |
| 5,947,977 A | 9/1999 | Slepian et al. | |
| 5,954,715 A | 9/1999 | Harrington et al. | |
| 5,955,143 A | 9/1999 | Wheatley et al. | |
| 5,962,006 A | 10/1999 | Southard et al. | |

(56) References Cited

U.S. PATENT DOCUMENTS

| | | | |
|---|---|---|---|
| 5,968,542 A | 10/1999 | Tipton |
| 5,972,002 A | 10/1999 | Bark et al. |
| 5,979,446 A | 11/1999 | Loy |
| 5,989,580 A | 11/1999 | Wallace et al. |
| 5,990,194 A | 11/1999 | Dunn et al. |
| 6,010,714 A | 1/2000 | Leung et al. |
| 6,019,757 A | 2/2000 | Scheldrup |
| 6,026,331 A | 2/2000 | Feldberg et al. |
| 6,037,331 A | 3/2000 | Shalaby et al. |
| 6,042,590 A | 3/2000 | Sporri et al. |
| 6,066,139 A | 5/2000 | Ryan et al. |
| 6,068,626 A | 5/2000 | Harrington et al. |
| 6,071,283 A | 6/2000 | Nardella et al. |
| 6,080,129 A | 6/2000 | Blaisdell |
| 6,080,152 A | 6/2000 | Nardella et al. |
| 6,096,052 A | 8/2000 | Callister et al. |
| 6,103,254 A | 8/2000 | Wallace et al. |
| 6,112,747 A | 9/2000 | Jones et al. |
| 6,113,614 A | 9/2000 | Mears |
| 6,120,789 A | 9/2000 | Dunn |
| 6,130,200 A | 10/2000 | Brodbeck et al. |
| 6,143,352 A | 11/2000 | Clark et al. |
| 6,145,505 A | 11/2000 | Nikolchev et al. |
| 6,152,943 A | 11/2000 | Sawhney |
| 6,165,492 A | 12/2000 | Neuwirth |
| 6,174,919 B1 | 1/2001 | Hickey |
| 6,176,240 B1 | 1/2001 | Nikolchev et al. |
| 6,179,832 B1 | 1/2001 | Jones et al. |
| 6,187,346 B1 | 2/2001 | Neuwirth |
| 6,196,966 B1 | 3/2001 | Kerin et al. |
| 6,197,351 B1 | 3/2001 | Neuwirth |
| 6,245,090 B1 | 6/2001 | Gilson et al. |
| 6,258,084 B1 | 7/2001 | Goldman et al. |
| 6,290,672 B1 | 9/2001 | Abae |
| 6,297,337 B1 | 10/2001 | Marchant et al. |
| 6,299,631 B1 | 10/2001 | Shalaby |
| 6,306,243 B1 | 10/2001 | Clark et al. |
| 6,309,384 B1 | 10/2001 | Harrington et al. |
| 6,327,505 B1 | 12/2001 | Medhkour et al. |
| 6,346,102 B1 | 2/2002 | Harrington et al. |
| 6,357,443 B1 | 3/2002 | Loy |
| 6,371,975 B2 | 4/2002 | Cruise et al. |
| 6,378,524 B1 | 4/2002 | Jones |
| 6,379,373 B1 | 4/2002 | Sawhney et al. |
| 6,395,293 B2 | 5/2002 | Poison et al. |
| 6,401,719 B1 | 6/2002 | Farley et al. |
| 6,413,536 B1 | 7/2002 | Gibson et al. |
| 6,413,539 B1 | 7/2002 | Shalaby |
| 6,432,116 B1 | 8/2002 | Callister et al. |
| 6,433,096 B1 | 8/2002 | Hickey et al. |
| 6,450,963 B1 | 9/2002 | Ackerman |
| 6,455,064 B1 | 9/2002 | Narang et al. |
| 6,458,147 B1 | 10/2002 | Cruise et al. |
| 6,461,631 B1 | 10/2002 | Dunn et al. |
| 6,465,001 B1 | 10/2002 | Hubbell et al. |
| 6,476,069 B2 | 11/2002 | Krall et al. |
| 6,476,070 B2 | 11/2002 | Krall et al. |
| 6,485,486 B1 | 11/2002 | Trembly et al. |
| RE37,950 E | 12/2002 | Dunn et al. |
| 6,493,589 B1 | 12/2002 | Medhkour et al. |
| 6,514,534 B1 | 2/2003 | Sawhney |
| 6,514,535 B2 | 2/2003 | Marchant |
| 6,526,979 B1 | 3/2003 | Nikolchev et al. |
| 6,528,080 B2 | 3/2003 | Dunn et al. |
| 6,538,026 B1 | 3/2003 | Krall et al. |
| 6,539,265 B2 | 3/2003 | Medhkour et al. |
| 6,550,480 B2 | 4/2003 | Feldman et al. |
| 6,565,557 B1 | 5/2003 | Sporri et al. |
| 6,577,903 B1 | 6/2003 | Cronin et al. |
| 6,579,469 B1 | 6/2003 | Nicholson et al. |
| 6,599,299 B2 | 7/2003 | Schultz |
| 6,605,294 B2 | 8/2003 | Sawhney |
| 6,605,667 B1 | 8/2003 | Badejo et al. |
| 6,607,631 B1 | 8/2003 | Badejo et al. |
| 6,610,033 B1 | 8/2003 | Melanson et al. |
| 6,620,846 B1 | 9/2003 | Jonn et al. |
| 6,634,361 B1 | 10/2003 | Nikolchev et al. |
| 6,635,055 B1 | 10/2003 | Cronin |
| 6,663,607 B2 | 12/2003 | Slaikeu et al. |
| 6,676,971 B2 | 1/2004 | Goupil et al. |
| 6,679,266 B2 | 1/2004 | Nikolchev et al. |
| 6,682,526 B1 | 1/2004 | Jones et al. |
| 6,684,884 B2 | 2/2004 | Nikolchev et al. |
| 6,689,148 B2 | 2/2004 | Sawhney et al. |
| 6,699,940 B2 | 3/2004 | Shalaby |
| 6,703,047 B2 | 3/2004 | Sawhney et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,723,144 B2 | 4/2004 | Katagiri et al. |
| 6,723,781 B1 | 4/2004 | Frate et al. |
| 6,726,682 B2 | 4/2004 | Harrington et al. |
| 6,736,822 B2 | 5/2004 | McClellan et al. |
| 6,743,248 B2 | 6/2004 | Edwards et al. |
| 6,752,803 B2 | 6/2004 | Goldman et al. |
| 6,758,831 B2 * | 7/2004 | Ryan .................. 604/103.03 |
| 6,763,833 B1 | 7/2004 | Khera et al. |
| 6,780,182 B2 | 8/2004 | Bowman et al. |
| 8,048,086 B2 | 11/2011 | Lee-Sepsick |
| 8,048,101 B2 | 11/2011 | Lee-Sepsick |
| 8,052,669 B2 | 11/2011 | Lee-Sepsick |
| 8,316,853 B2 | 11/2012 | Lee-Sepsick |
| 8,316,854 B2 | 11/2012 | Lee-Sepsick |
| 8,324,193 B2 | 12/2012 | Lee-Sepsick |
| 8,336,552 B2 | 12/2012 | Lee-Sepsick |
| 8,695,606 B2 | 4/2014 | Lee-Sepsick |
| 8,726,906 B2 | 5/2014 | Lee-Sepsick |
| 2001/0016738 A1 | 8/2001 | Harrington et al. |
| 2001/0016739 A1 | 8/2001 | Goldman et al. |
| 2001/0023365 A1 | 9/2001 | Medhkour et al. |
| 2001/0041900 A1 | 11/2001 | Callister et al. |
| 2002/0013589 A1 | 1/2002 | Callister et al. |
| 2002/0020417 A1 | 2/2002 | Nikolchev et al. |
| 2002/0029051 A1 | 3/2002 | Callister et al. |
| 2002/0035101 A1 | 3/2002 | Dey et al. |
| 2002/0072744 A1 | 6/2002 | Harrington et al. |
| 2002/0082636 A1 | 6/2002 | Sawhney et al. |
| 2002/0095082 A1 | 7/2002 | Evans et al. |
| 2002/0106411 A1 | 8/2002 | Wironen et al. |
| 2002/0133140 A1 | 9/2002 | Moulis |
| 2002/0148476 A1 | 10/2002 | Farley et al. |
| 2002/0176893 A1 | 11/2002 | Wironen et al. |
| 2002/0177846 A1 | 11/2002 | Mulier et al. |
| 2002/0177855 A1 | 11/2002 | Greene, Jr. et al. |
| 2003/0015203 A1 | 1/2003 | Makower et al. |
| 2003/0029457 A1 | 2/2003 | Callister et al. |
| 2003/0051735 A1 | 3/2003 | Pavcnik et al. |
| 2003/0060800 A1 | 3/2003 | Ryan |
| 2003/0066533 A1 | 4/2003 | Loy |
| 2003/0082636 A1 | 5/2003 | Wong |
| 2003/0108586 A1 | 6/2003 | Ramey |
| 2003/0134032 A1 | 7/2003 | Chaouk et al. |
| 2003/0158563 A1 | 8/2003 | McClellan et al. |
| 2003/0170173 A1 | 9/2003 | Klaveness et al. |
| 2003/0171759 A1 | 9/2003 | Sadler et al. |
| 2003/0185896 A1 | 10/2003 | Buiser et al. |
| 2003/0194389 A1 | 10/2003 | Porter |
| 2003/0194390 A1 | 10/2003 | Krall et al. |
| 2003/0223956 A1 | 12/2003 | Goupil et al. |
| 2004/0002680 A1 | 1/2004 | Ackerman et al. |
| 2004/0079377 A1 | 4/2004 | Nikolchev et al. |
| 2004/0127918 A1 | 7/2004 | Nikolchev et al. |
| 2004/0159324 A1 | 8/2004 | Nikolchev et al. |
| 2004/0161384 A1 | 8/2004 | Wheatley et al. |
| 2004/0163650 A1 | 8/2004 | Lowe et al. |
| 2004/0204720 A1 | 10/2004 | Harrington et al. |
| 2004/0206358 A1 | 10/2004 | Nikolchev et al. |
| 2004/0211429 A1 | 10/2004 | Nikolchev et al. |
| 2004/0215215 A1 | 10/2004 | McClellan et al. |
| 2004/0241874 A1 | 12/2004 | Abdel-Rehim |
| 2004/0258761 A1 | 12/2004 | Wheatley et al. |
| 2004/0258769 A1 | 12/2004 | Barker et al. |
| 2005/0045183 A1 * | 3/2005 | Callister et al. .................. 128/831 |
| 2005/0187561 A1 * | 8/2005 | Lee-Sepsick et al. .......... 606/108 |

(56) References Cited

U.S. PATENT DOCUMENTS

| | | | |
|---|---|---|---|
| 2005/0240211 | A1 | 10/2005 | Sporri et al. |
| 2006/0178620 | A1 | 8/2006 | Wollmann et al. |
| 2008/0063603 | A1 | 3/2008 | Schneider et al. |
| 2008/0264865 | A1 | 10/2008 | Herman |
| 2009/0024108 | A1 | 1/2009 | Lee-Sepsick et al. |
| 2009/0024155 | A1 | 1/2009 | Lee-Sepsick et al. |
| 2009/0277455 | A1 | 11/2009 | Lee-Sepsick et al. |
| 2009/0306623 | A1 | 12/2009 | McIntosh et al. |
| 2011/0135307 | A1 | 6/2011 | Conner et al. |
| 2012/0042879 | A1 | 2/2012 | Lee-Sepsick et al. |
| 2012/0046260 | A1 | 2/2012 | Lee-Sepsick et al. |
| 2013/0220334 | A1 | 8/2013 | Lee-Sepsick |
| 2013/0220335 | A1 | 8/2013 | Lee-Sepsick |
| 2013/0225977 | A1 | 8/2013 | Lee-Sepsick |
| 2014/0039639 | A1 | 2/2014 | Lee-Sepsick |

FOREIGN PATENT DOCUMENTS

| | | |
|---|---|---|
| DE | 2537620 | 2/1977 |
| DE | 3324754 | 7/1983 |
| DE | 1722732 | 3/2013 |
| EP | 05723981.6 | 2/2005 |
| EP | 13155297.8 | 2/2013 |
| EP | 1722732 | 3/2013 |
| FR | 2414925 | 8/1979 |
| GB | 1470571 | 4/1977 |
| GB | 1722732 | 3/2013 |
| HK | 07105332.9 | 2/2005 |
| HK | 1098042 A | 7/2007 |
| IE | 1722732 | 3/2013 |
| IN | 2536/KOLNP/06 | 2/2005 |
| JP | 59-046500 | 3/1984 |
| JP | 2002-200176 | 7/2002 |
| JP | 2007-500782 | 2/2005 |
| JP | 4750782 | 5/2011 |
| WO | WO 81/00701 | 3/1981 |
| WO | WO 88/09648 | 12/1988 |
| WO | WO 93/14786 | 8/1993 |
| WO | WO 94/24944 | 11/1994 |
| WO | WO 94/28803 | 12/1994 |
| WO | WO 95/19184 | 7/1995 |
| WO | WO 95/25490 | 9/1995 |
| WO | WO 97/12569 | 4/1997 |
| WO | WO 97/42987 | 11/1997 |
| WO | WO 97/49345 | 12/1997 |
| WO | WO 98/26737 | 6/1998 |
| WO | WO 98/31308 | 7/1998 |
| WO | WO 99/07297 | 2/1999 |
| WO | WO 99/47073 | 9/1999 |
| WO | WO 00/18469 | 4/2000 |
| WO | WO 00/24374 | 5/2000 |
| WO | WO 00/44323 | 8/2000 |
| WO | WO 00/54746 | 9/2000 |
| WO | WO 01/37760 | 5/2001 |
| WO | WO 02/39880 | 5/2002 |
| WO | WO 02/47744 | 6/2002 |
| WO | WO 03/070085 | 3/2003 |
| WO | WO 2004/024237 | 3/2004 |
| WO | WO 2004/035022 | 4/2004 |
| WO | WO 2005/082299 | 9/2005 |

OTHER PUBLICATIONS

Risquez, Human Reproduction, 5, 6, 1990.*
El-Mowafi DM, et al. (2008) Fallopian Tube. Geneva Foundation for Medical Education and Research. (8 pages) Download available at: http://www.gfmer.ch/International_activities_En/El_Mowafi/Fallopian_tube.htm.
Keller MW, et al. (1986) Automated production and analysis of echo contrast agents. J Ultrasound Med. 5(9): 493-498.
Abdala N, et al. (2001). Use of ethylene vinyl alcohol copolymer for tubal sterilization by selective catheterization in rabbits. J Vasc Interv Radiol. 12(8): 979-984.
Abma JC, et al. (1997) Fertility, family planning, and women's health: new data from the 1995 National Survey of Family Growth. Vital Health Stat 23. (19): 1-114.
American Foundation for Urologic Disease. (2005) Facts about vasectomy safety. Published by the National Institute of Child Health & Human Development. Retrieved on Jun. 29, 2005 from the world wide web at http://www.nichd.nih.gov/publications/pubs/vasect.htm.
ApSimon HT, et al. (1984) Embolization of small vessels with a double-lumen microballoon catheter. Part I: Design and construction. Radiology. 151(1): 55-57.
Assaf A, et al. (1993) Histopathological effects of silicone rubber 'Ovabloc' on the human fallopian tube. Int J Gynaecol Obstet. 43(2): 181-189.
Basu S, et al. (1995) Comparative study of biological glues: cryoprecipitate glue, two-component fibrin sealant, and "French" glue. Ann Thorac Surg. 60(5): 1255-1262.
Berkey GS, et al. (1995) Sterilization with methyl cyanoacrylate-induced fallopian tube occlusion from a nonsurgical transvaginal approach in rabbits. J Vasc Interv Radiol. 6(5): 669-674.
Brundin J, et al. (1985) Long-term toxicity of a hydrogelic occlusive device in the isthmus of the human oviduct. A light microscopic study. Acta Pathol Microbiol Immunol Scand A. 93(3): 121-126.
Brundin J. (1991) Transcervical sterilization in the human female by hysteroscopic application of hydrogelic occlusive devices into the intramural parts of the fallopian tubes: 10 years experience of the P-block. Eur J Obstet Gynecol Reprod Biol. 39(1): 41-49.
Canavan TP. (1998) Appropriate use of the intrauterine device. Am Fam Physician. 58(9): 2077-2084, 2087-2088.
Chen FQ. (1989) Study on the transperitoneal sterilization of the fallopian tube with silicon rubber plug and its reversibility. Shengzhi Yu Biyun. 9(3): 51-54.
Clenney TL, et al. (1999) Vasectomy techniques. Am Fam Physician. 60(1): 137-146, 151-152.
Cooper JM. (1992) Hysteroscopic sterilization. Clin Obstet Gynecol. 35(2): 282-298.
Dan SJ, et al. (1984) Fallopian tube occlusion with silicone: radiographic appearance. Radiology. 151(3): 603-605.
Davis RH, et al. (1975) Fallopian tube occlusion in rabbits with silicone rubber. J Reprod Med. 14(2): 56-61.
Davis RH, et al. (1979) Chronic occlusion of the monkey fallopian tube with silicone polymer. Obstet Gynecol. 53(4): 527-529.
Davis RH, et al. (1979) Chronic occlusion of the rabbit Fallopian tube with silicone polymer. Gynecol Obstet Invest. 10(6): 281-288.
Erb RA, et al. (1979) Hysteroscopic oviductal blocking with formed-in-place silicone rubber plugs. I. Method and apparatus. J Reprod Med. 23(2): 65-68.
Farcon E, et al. (1975) An absorbable intravasal stent and a silicone intravasal reversible plug. Report of experiments on animals. Invest Urol. 13(2): 108-112.
Fischer ME, et al. (1984) Silicone devices for tubal occlusion: radiographic description and evaluation. Radiology. 151(3): 601-602.
Grode GA, et al. (1971) Feasibility study on the use of a tissue adhesive for the nonsurgical blocking of fallopian tubes. Phase I: evaluation of a tissue adhesive. Fertil Steril. 22(9): 552-555.
Harrell WB, et al. (1969) Simulated tuboplasty using tissue adhesive on uterine horn in canines. J Ark Med Soc. 65(11): 433-435.
Hefnawi F, et al. (1967) Control of fertility by temporary occlusion of the oviduct. Am J Obstet Gynecol. 99(3): 421-427.
Hendrix NW, et al. (1999). Sterilization and its consequences. Obstet Gynecol Surv. 54(12): 766-777.
Holt VL, et al. (2003) Oral contraceptives, tubal sterilization, and functional ovarian cyst risk. Obstet Gynecol. 102(2): 252-258.
Huvar I, et al. (1994) Hysteroscopic sterilization using Ovabloc. Ceska Gynekol. 59(4): 193-195.
Jamieson DJ, et al. (2002) A comparison of women's regret after vasectomy versus tubal sterilization. Obstet Gynecol. 99(6): 1073-1079.
Libenzon LL, et al. (1973) Contraception through the sealing off of Fallopian tubes (experimental studies). Eksp Khir Anesteziol. 18(5): 18-20.
Loffer FD, et al. (1986) Learning hysteroscopy sterilization and the Ovabloc System with Hyskon. Acta Eur Fertil. 17(6): 477-480.

(56) References Cited

OTHER PUBLICATIONS

Loffer FD. (1982) What's new in female sterilization? The silicone tubal plug is. Ariz Med. 39(7): 442-445.
Loffer FD. (1984) Hysteroscopic sterilization with the use of formed-in-place silicone plugs. Am J Obstet Gynecol. 149(3): 261-270.
Maubon AJ, et al. (1996) Tubal sterilization by means of selective catheterization: comparison of a hydrogel and a collagen glue. J Vasc Intery Radiol. 7(5): 733-736.
Neuwirth RS, et al. (1971) Chemical induction of tubal blockade in the monkey. Obstet Gynecol. 38(1): 51-54.
Neuwirth RS, et al. (1980) An outpatient approach to female sterilization with methylcyanoacrylate. Am J Obstet Gynecol. 136(7): 951-956.
Neuwirth RS, et al. (1983) Trials with the FEMCEPT method of female sterilization and experience with radiopaque methylcyanoacrylate. Am J Obstet Gynecol. 145(8): 948-954.
No authors listed. (1973) Animal studies show silicone plugs prevent conception. JAMA. 225(2): 105-106.
No authors listed. (1973) Implants seen as reversible contraceptives. Biomed News. 4: 12.
No authors listed. (Apr. 1994) Hysteroscopy. ACOG Technical Bulletin No. 191. Int J Gynaecol Obstet. 45(2): 175-180.
Omran KF, et al. (1970) Tubal occlusion: a comparative study. Int J Fertil. 15(4): 226-241.
Pelage JP, et al. (1998) Selective salpingography and fallopian tubal occlusion with n-butyl-2-cyanoacrylate: report of two cases. Radiology. 207(3): 809-812.
Pollack A. (2003) ACOG practice bulletin. Clinical management guidelines for obstetrician-gynecologists. Obstet Gynecol. 102(3): 647-658.
Rakshit B. (1970) Attempts at chemical blocking of the Fallopian tube for female sterilization. J Obstet Gynaecol India. 20: 618-624.
Reed TP et al. (1980) Tubal occlusion with silicone rubber: an update. J Reprod Med. 25(1): 25-28.
Reed TP, et al. (1983) Hysteroscopic tubal occlusion with silicone rubber. Obstet Gynecol. 61(3): 388-392.
Reed TP, et al. (Nov. 1978) Hysteroscopic Oviductal Blocking with Formed-In-Place Silicone Rubber Plugs Clinical Studies. Paper presented at the Clinical Symposium on Gynecologic Endoscopy. 7th Annual Meeting (Hollywood, FL) (pp. 1-4).
Richart RM. (1981) Female sterilization using chemical agents. Res Front Fertil Regul. 1(5): 1-12.
Richman TS, et al. (1984) Fallopian tubal patency assessed by ultrasound following fluid injection. Radiology. 152(2): 507-510.
Saito H, et al. (2007) pH-responsive swelling behavior of collagen gels prepared by novel crosslinkers based on naturally derived di- or tricarboxylic acids. Acta Biomater. 3(1): 89-94.
Snider S. (1990). The Pill: 30 years of Safety Concerns. Published by the U.S. Food and Drug Administration. (6 pages).
Steptoe PC. (1975) Advances in laparoscopic sterilisation techniques. S Afr Med J. 49(48): 2019-2021.
Stevenson TC, et al. (1972) The effect of methyl cyanoacrylate tissue adhesive on the human Fallopian tube and endometrium. J Obstet Gynaecol Br Commonw. 79(11): 1028-1039.
Su YK. (1991) Embolus formation using bismuth polyurethane for tubosterilization observation of 259 cases. Zhonghua Fu Chan Ke Za Zhi. 26(6): 352-354, 388.
United Nations Secretariat. (2003) Fertility, Contraception and population policies. United Nations Population Division, Department of Economic and Social Affairs. ESA/P/WP.182 (42 pages).
van der Leij G, et al. (1995) Impact of Ovabloc intratubal polymer on the morphology of the fallopian tube. Int J Gynecol Pathol. 14(2): 167-173.
van der Leij G, et al. (1997) Radiographic aspects of office hysteroscopic tubal occlusion with siloxane intratubal devices (the Ovabloc method). Int J Gynaecol Obstet. 59(2): 123-131.
Viddya Medical News Service. (2000) Bibliography Excerpts: Side effects of tubal ligation sterilizations. 1: 249. (5 pages).
Volpi E, et al. (1996). Transvaginal sonographic tubal patency testing using air and saline solution as contrast media in a routine infertility clinic setting. Ultrasound Obstet Gynecol. 7(1): 43-48.
Wilson EW. (1995) The evolution of methods for female sterilization. Int J Gynaecol Obstet. 51 Suppl 1: S3-13.
Issue Notification issued Oct. 12, 2011 for U.S. Appl. No. 11/065,886, filed Feb. 24, 2005 (Lee-Sepsick et al.—inventors) (1 page).
Notice of Allowance issued Jul. 15, 2011 for U.S. Appl. No. 11/065,886, filed Feb. 24, 2005 (Lee-Sepsick et al.—inventors) (11 pages).
Response to Non-Final Office Action filed Apr. 19, 2011 for U.S. Appl. No. 11/065,886, filed Feb. 24, 2005 (Lee-Sepsick et al.—inventors) (17 pages).
Draft Claim Language faxed Mar. 15, 2011 for U.S. Appl. No. 11/065,886, filed Feb. 24, 2005 (Lee-Sepsick et al.—inventors) (4 pages).
Non-Final Office Action issued Jan. 19, 2011 for U.S. Appl. No. 11/065,886, filed Feb. 24, 2005 (Lee-Sepsick et al.—inventors) (25 pages).
Response to Final Office Action filed Sep. 23, 2010 for U.S. Appl. No. 11/065,886, filed Feb. 24, 2005 (Lee-Sepsick et al.—inventors) (30 pages).
Advisory Action issued Jul. 15, 2010 for U.S. Appl. No. 11/065,886, filed Feb. 24, 2005 (Lee-Sepsick et al.—inventors) (8 pages).
Response to Final Office Action filed Jun. 24, 2010 for U.S. Appl. No. 11/065,886, filed Feb. 24, 2005 (Lee-Sepsick et al.—inventors) (26 pages).
Notice of Appeal filed Jun. 24, 2010 for U.S. Appl. No. 11/065,886, filed Feb. 24, 2005 (Lee-Sepsick et al.—inventors) (1 page).
Examiner Interview Summary issued May 25, 2010 for U.S. Appl. No. 11/065,886, filed Feb. 24, 2005 (Lee-Sepsick et al.—inventors) (4 pages).
Final Office Action issued Dec. 24, 2009 for U.S. Appl. No. 11/065,886, filed Feb. 24, 2005 (Lee-Sepsick et al.—inventors) (29 pages).
Response to Non-Final Office Action filed Sep. 24, 2009 U.S. Appl. No. 11/065,886, filed Feb. 24, 2005 (Lee-Sepsick et al.—inventors) (22 pages).
Examiner Interview Summary issued Jun. 30, 2009 for U.S. Appl. No. 11/065,886, filed Feb. 24, 2005 (Lee-Sepsick et al.—inventors) (2 pages).
Non-Final Office Action issued Jun. 24, 2009 for U.S. Appl. No. 11/065,886, filed Feb. 24, 2005 (Lee-Sepsick et al.—inventors) (26 pages).
Response to Restriction Requirement filed Apr. 21, 2009 for U.S. Appl. No. 11/065,886, filed Feb. 24, 2005 (Lee-Sepsick et al.—inventors) (10 pages).
Restriction Requirement issued Mar. 23, 2009 for U.S. Appl. No. 11/065,886, filed Feb. 24, 2005 (Lee-Sepsick et al.—inventors) (5 pages).
Issue Notification issued Oct. 12, 2011 for U.S. Appl. No. 12/240,738, filed Sep. 29, 2008 (Lee-Sepsick et al.—inventors) (1 page).
Notice of Allowance and Fee(s) Due issued Jul. 25, 2011 for U.S. Appl. No. 12/240,738, filed Sep. 29, 2008 (Lee-Sepsick et al.—inventors) (9 pages).
Terminal Disclaimer (with Review) filed Jul. 10, 2011 for U.S. Appl. No. 12/240,738, filed Sep. 29, 2008 (Lee-Sepsick et al.—inventors) (3 pages).
Terminal Disclaimer (with Review) filed Jun. 24, 2011 for U.S. Appl. No. 12/240,738, filed Sep. 29, 2008 (Lee-Sepsick et al.—inventors) (3 pages).
Response to Non-Final Office Action filed Apr. 21, 2011 for U.S. Appl. No. 12/240,738, filed Sep. 29, 2008 (Lee-Sepsick et al.—inventors) (15 pages).
Non-Final Office Action issued Dec. 21, 2010 for U.S. Appl. No. 12/240,738, filed Sep. 29, 2008 (Lee-Sepsick et al.—inventors) (22 pages).
Response to Restriction Requirement filed Oct. 11, 2010 for U.S. Appl. No. 12/240,738, filed Sep. 29, 2008 (Lee-Sepsick et al.—inventors) (7 pages).

(56) References Cited

OTHER PUBLICATIONS

Restriction Requirement issued Jun. 9, 2010 for U.S. Appl. No. 12/240,738, filed Sep. 29, 2008 (Lee-Sepsick et al.—inventors) (6 pages).
Issue Notification issued Oct. 19, 2010 for U.S. Appl. No. 12/240,791, filed Sep. 29, 2008 (Lee-Sepsick et al.—inventors) (1 page).
Notice of Allowance issued Jul. 21, 2011 for U.S. Appl. No. 12/240,791, filed Sep. 29, 2008 (Lee-Sepsick et al.—inventors) (12 pages).
Terminal Disclaimer (with Review) filed Jun. 24, 2011 for U.S. Appl. No. 12/240,791, filed Sep. 29, 2008 (Lee-Sepsick et al.—inventors) (3 pages).
Response to Non-Final Office Action filed Apr. 21, 2011 for U.S. Appl. No. 12/240,791, filed Sep. 29, 2008 (Lee-Sepsick et al.—inventors) (10 pages).
Non-Final Office Action issued Dec. 21, 2010 for U.S. Appl. No. 12/240,791, filed Sep. 29, 2008 (Lee-Sepsick et al.—inventors) (15 pages).
Response to Restriction Requirement filed Oct. 11, 2010 for U.S. Appl. No. 12/240,791, filed Sep. 29, 2008 (Lee-Sepsick et al.—inventors) (6 pages).
Restriction Requirement issued Jun. 9, 2010 for U.S. Appl. No. 12/240,791, filed Sep. 29, 2008 (Lee-Sepsick et al.—inventors) (6 pages).
Issue Notification issued Nov. 7, 2012 for U.S. Appl. No. 12/504,912, filed Jul. 17, 2009 (Lee-Sepsick et al.—inventors) (1 page).
Miscellaneous Communication issued Oct. 25, 2012 for U.S. Appl. No. 12/504,912, filed Jul. 17, 2009 (Lee-Sepsick et al.—inventors) (2 pages).
Response to Rule 1.312 Amendment mailed Sep. 17, 2012 for U.S. Appl. No. 12/504,912, filed Jul. 17, 2009(Inventors—Lee-Sepsick et al.) (2 pages).
Rule 1.312 Amendment filed Aug. 28, 2012 for U.S. Appl. No. 12/504,912, filed Jul. 17, 2009 (Inventors—Lee-Sepsick et al.) (3 pages).
Notice of Allowance mailed Jul. 19, 2012 for U.S. Appl. No. 12/504,912, filed Jul. 17, 2009 (Inventors—Lee-Sepsick et al.) (7 pages).
Notice of Allowance mailed Mar. 14, 2012 for U.S. Appl. No. 12/504,912, filed Jul. 17, 2009 (Inventors—Lee-Sepsick et al.) (9 pages).
Terminal Disclaimer (with Review) filed Feb. 9, 2012 for U.S. Appl. No. 12/504,912, filed Jul. 17, 2009 (Lee-Sepsick et al.—inventors) (15 pages).
Response to Final Office Action filed Feb. 9, 2012 for U.S. Appl. No. 12/504,912, filed Jul. 17, 2009 (Lee-Sepsick et al.—inventors) (6 pages).
Final Office Action issued Jan. 6, 2012 for U.S. Appl. No. 12/504,912, filed Jul. 17, 2009 (Lee-Sepsick et al.—inventors) (9 pages).
Response to Non-Final Office Action filed Nov. 4, 2011 for U.S. Appl. No. 12/504,912, filed Jul. 17, 2009 (Lee-Sepsick et al.—inventors) (10 pages).
Non-Final Office Action issued Aug. 4, 2011 for U.S. Appl. No. 12/504,912, filed Jul. 17, 2009 (Lee-Sepsick et al.—inventors) (15 pages).
Issue Notification issued Nov. 7, 2012 for U.S. Appl. No. 13/285,744, filed Oct. 31, 2011 (Lee-Sepsick et al.—inventors (1 page).
Response to Rule 1.312 Amendment mailed Sep. 17, 2012 for U.S. Appl. No. 13/285,744, filed Oct. 31, 2011 (Inventors—Lee-Sepsick et al.) (2 pages).
Rule 1.312 Amendment filed Aug. 28, 2012 for U.S. Appl. No. 13/285,744, filed Oct. 31, 2011 (Inventors—Lee-Sepsick et al.) (3 pages).
Notice of Allowance mailed Jul. 25, 2012 for U.S. Appl. No. 13/285,744, filed Oct. 31, 2011 (Inventors—Lee-Sepsick et al.) (7 pages).

Terminal Disclaimers (with Review) mailed Jul. 2, 2012 for U.S. Appl. No. 13/285,744, filed Oct. 31, 2011 (Inventors—Lee-Sepsick et al.) (4 pages).
Response to Final Office Action mailed Jul. 2, 2012 for U.S. Appl. No. 13/285,744, filed Oct. 31, 2011 (Inventors—Lee-Sepsick et al.) (7 pages).
Final Office Action mailed Mar. 30, 2012 for U.S. Appl. No. 13/285,744, filed Oct. 31, 2011 (Inventors—Lee-Sepsick et al.) (8 pages).
Terminal Disclaimers (with Review) mailed Mar. 16. 2012 for U.S. Appl. No. 13/285,744, filed Oct. 31, 2011 (Inventors—Lee-Sepsick et al.) (3 pages).
Response to Non-Final Office Action mailed Mar. 16, 2012 for U.S. Appl. No. 13/285,744, filed Oct. 31, 2011(Inventors—Lee-Sepsick et al.) (8 pages).
Non-Final Office Action issued Feb. 17, 2012 for U.S. Appl. No. 13/285,744, filed Oct. 31, 2011 (Lee-Sepsick et al.—inventors) (11 pages).
Preliminary Amendment filed Oct. 31, 2011 for U.S. Appl. No. 13/285,744, filed Oct. 31, 2011 (Lee-Sepsick et al.—inventors) (7 pages).
Issue Notification issued Dec. 5, 2012 for U.S. Appl. No. 13/285,908, filed Oct. 31, 2011 (Lee-Sepsick et al.—inventors) (1 page).
Notice of Allowability issued Nov. 2, 2012 for U.S. Appl. No. 13/285,908, filed Oct. 31, 2011 (Lee-Sepsick et al.—inventors) (7 pages).
Notice of Allowance and Fees Due issued Sep. 4, 2012 for U.S. Appl. No. 13/285,908, filed Oct. 31, 2011 (Lee-Sepsick et al.—inventors) (9 pages).
Response to Non-Final Office Action with Terminal Disclaimers (and Review) filed Jul. 26, 2012 for U.S. Appl. No. 13/285,908, filed Oct. 31, 2011 (Lee-Sepsick et al.—inventors) (12 pages).
Non-Final Office Action issued Apr. 26, 2012 for U.S. Appl. No. 13/285,908, filed Oct. 31, 2011 (Lee-Sepsick et al.—inventors) (9 pages).
Preliminary Amendment filed Oct. 31, 2011 for U.S. Appl. No. 13/285,908, filed Oct. 31, 2011 (Lee-Sepsick et al.—inventors) (7 pages).
Issue Notification issued Nov. 14, 2012 for U.S. Appl. No. 13/286,127, filed Oct. 31, 2011 (Lee-Sepsick et al.—inventors) (1 page).
Response to Rule 1.312 Amendments mailed Sep. 17, 2012 for U.S. Appl. No. 13/286,127, filed Oct. 31, 2011 (Inventors—Lee-Sepsick et al.) (2 pages).
Second Rule 1.312 Amendment filed Aug. 29, 2012 for U.S. Appl. No. 13/286,127, filed on Oct. 31, 2011(Inventors—Lee-Sepsick et al.) (2 pages).
Rule 1.312 Amendment filed Aug. 28, 2012 for U.S. Appl. No. 13/286,127, filed Oct. 31, 2011 (Inventors—Lee-Sepsick et al.) (3 pages).
Notice of Allowance mailed Aug. 8, 2012 for U.S. Appl. No. 13/286,127, filed Oct. 31, 2011 (Inventors—Lee-Sepsick et al.) (8 pages).
Terminal Disclaimers (with Review) filed Jul. 2, 2012 for U.S. Appl. No. 13/286,127, filed Oct. 31, 2011 (Inventors—Lee-Sepsick et al.) (5 pages).
Response to Non-Final Rejection filed Jul. 2, 2012 for U.S. Appl. No. 13/286,127, filed Oct. 31, 2011 (Inventors—Lee-Sepsick et al.) (5 pages).
Non-Final Rejection mailed Mar. 30, 2012 for U.S. Appl. No. 13/286,127, filed Oct. 31, 2011 (Inventors—Lee-Sepsick et al.) (8 pages).
Preliminary Amendment filed Oct. 31, 2011 for U.S. Appl. No. 13/286,127, filed Oct. 31, 2011 (Lee-Sepsick et al.—inventors) (7 pages).
Issue Fee Transmittal filed Feb. 15, 2014 for U.S. Appl. No. 13/684,524, filed Nov. 24, 2012 (Inventors—Lee-Sepsick et al.) (2 pages).
Notice of Allowance and Fee(s) Due mailed Nov. 15, 2013 for U.S. Appl. No. 13/684,524, filed Nov. 24, 2012 (Inventors—Lee-Sepsick et al.) (9 pages).

(56) References Cited

OTHER PUBLICATIONS

Response to Non-Final Office Action with Terminal Disclaimers filed Oct. 21, 2013 for U.S. Appl. No. 13/684,524, filed Nov. 24, 2012 (Inventors—Lee-Sepsick et al.) (9 pages).
Non-Final Rejection issued Jul. 19, 2013 for U.S. Appl. No. 13/684,524, filed Nov. 24, 2012 (Inventors—Lee-Sepsick et al.) (9 pages).
Preliminary Amendment filed May 14, 2013 for U.S. Appl. No. 13/684,524, filed Nov. 24, 2012 (Inventors—Lee-Sepsick et al.) (6 pages).
Notice of Allowance mailed Jan. 16, 2015 for U.S. Appl. No. 13/684,529, filed Nov. 24, 2012 (Inventors—Lee-Sepsick et al.) (8 pages).
Response to Final Rejection with Terminal Disclaimer filed Dec. 11, 2014 for U.S. Appl. No. 13/684,529, filed Nov. 24, 2012 (Inventors—Lee-Sepsick et al.) (9 pages).
Final Rejection mailed Oct. 23, 2014 for U.S. Appl. No. 13/684,529, filed Nov. 24, 2012 (Inventors—Lee-Sepsick et al.) (10 pages).
Response to Non-Final Rejection filed Jul. 3, 2014 for U.S. Appl. No. 13/684,529, filed Nov. 24, 2012 (Inventors—Lee-Sepsick et al.) (16 pages).
Non-Final Rejection mailed Jan. 3, 2014 for U.S. Appl. No. 13/684,529, filed Nov. 24, 2012 (Inventors—Lee-Sepsick et al.) (17 pages).
Response to Notice to File Missing Parts and Preliminary Amendment filed May 16, 2013 for U.S. Appl. No. 13/684,529, filed Nov. 24, 2012 (Inventors—Lee-Sepsick et al.) (7 pages).
Issue Notification mailed Apr. 30, 2014 for U.S. Appl. No. 13/684,546, filed Nov. 25, 2012 (Inventors—Lee-Sepsick et al.) (1 page).
Corrected Notice of Allowability mailed Apr. 15. 2014 for U.S. Appl. No. 13/684,546, filed Nov. 25, 2012 (Inventors—Lee-Sepsick et al.) (2 pages).
Notice of Allowance mailed Dec. 23, 2013 for U.S. Appl. No. 13/684,546, filed Nov. 25, 2012 (Inventors—Lee-Sepsick et al.) (9 pages).
Response to Non-Final Rejection and Terminal Disclaimer filed Dec. 6, 2013 for U.S. Appl. No. 13/684,546, filed Nov. 25, 2012 (Inventors—Lee-Sepsick et al.) (10 pages).
Non-Final Rejection mailed Sep. 6, 2013 for U.S. Appl. No. 13/684,546, filed Nov. 25, 2012 (Inventors—Lee-Sepsick et al.) (10 pages).
Response to Notice to File Missing Parts and Preliminary Amendment filed May 14, 2013 for U.S. Appl. No. 13/684,546, filed Nov. 25, 2012 (Inventors—Lee-Sepsick et al.) (7 pages).
Preliminary Amendment filed May 14, 2013 for U.S. Appl. No. 13/684,549, filed Nov. 25, 2012 (Inventors—Lee-Sepsick et al.) (7 pages).
Request for Reconsideration of the Holding of Abandonment filed Nov. 26, 2014 for U.S. Appl. No. 14/196,491, filed Mar. 4, 2014 (Inventors—Lee-Sepsick et al.) (10 pages).
Notice of Abandonment mailed Oct. 30, 2014 for U.S. Appl. No. 14/196,491, filed Mar. 4, 2014 (Inventors—Lee-Sepsick et al.) (2 pages).
Preliminary Amendment filed Oct. 24, 2014 for U.S. Appl. No. 14/196,491, filed Mar. 4, 2014 (Inventors—Lee-Sepsick et al.) (5 pages).
Preliminary Amendment filed Mar. 4, 2014 for U.S. Appl. No. 14/196,491, filed Mar. 4, 2014 (Inventors—Lee-Sepsick et al.) (3 pages).
Response to Third Office Action filed Sep. 6, 2010 for Chinese Application No. CN 200580006068.X, which claims priority to PCT/US2005/006334 filed on Feb. 25, 2005 (Lee-Sepsick et al. listed as inventors and Femasys Inc. listed as Applicant).
Third Office Action issued Jun. 24, 2010 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to Second Office Action filed Apr. 24, 2009 for Chinese Application No. CN 200580006068.X, which claims priority to PCT/US2005/006334 filed on Feb. 25, 2005 (Lee-Sepsick et al. listed as inventors and Femasys Inc. listed as Applicant).
Second Office Action issued Dec. 12, 2008 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to First Office Action filed Jun. 16, 2008 for Chinese Application No. CN 200580006068.X, which claims priority to PCT/US2005/006334 filed on Feb. 25, 2005 (Lee-Sepsick et al. listed as inventors and Femasys Inc. listed as Applicant).
First Office Action issued Nov. 30, 2007 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to Examination Report filed Oct. 12, 2012 for Canadian Application No. CA 2556747, which claims priority to PCT/US2005/006334 filed on Feb. 25, 2005 (Lee-Sepsick et al.—inventors; Femasys Inc.—Applicant) (5 pages).
Examination Report filed Jun. 7, 2012 for Canadian Application No. CA 2556747, which claims priority to PCT/US2005/006334 filed on Feb. 25, 2005 (Lee-Sepsick et al.—inventors; Femasys Inc.—Applicant) (2 pages).
Response to Examination Report filed May 7, 2012 for Canadian Application No. CA 2556747, which claims priority to PCT/US2005/006334 filed on Feb. 25, 2002 (Lee-Sepsick et al.—inventors; Femasys Inc.—Applicant) (12 pages).
Examination Report issued Nov. 8, 2011 for Canadian Application No. CA 2556747, which claims priority to PCT/US2005/006334 filed on Feb. 25, 2005 (Lee-Sepsick et al.—inventors; Femasys Inc.—Applicant) (2 pages).
Amended Claims filed Oct. 19, 2011 for Canadian Application No. CA 2556747, which claims priority to PCT/US2005/006334 filed on Feb. 25, 2005 (Lee-Sepsick et al.—inventors; Femasys Inc.—Applicant) (11 pages).
Examination Report issued Apr. 19, 2011 for Canadian Application No. CA 2556747, which claims priority to PCT/US2005/006334 filed on Feb. 25, 2005 (Lee-Sepsick et al.—inventors; Femasys Inc.—Applicant) (3 pages).
Voluntary Amendments filed Mar. 1, 2010 for Canadian Application No. CA 2556747, which claims priority to PCT/US2005/006334 filed on Feb. 25, 2005 (Lee-Sepsick et al. listed as inventors and Femasys Inc. listed as Applicant) (16 pages).
Certificate of Grant issue Mar. 27, 2013 for European Patent Application No. 05723981.3, which claims priority to PCT/US2005/006334 filed on Feb. 25, 2005 (Lee-Sepsick et al.—inventors; Femasys Inc.—Applicant) (1 page).
Communication under Rule 71(3) EPC issued Oct. 12, 2012 for European Patent Application No. 05723981.3, which claims priority to PCT/US2005/006334 filed on Feb. 25, 2005 (Lee-Sepsick et al.—inventors; Femasys Inc.—Applicant) (8 pages).
Response to Article 94(3) Communication filed Feb. 6, 2012 for European Patent Application No. 05723981.3, which claims priority to PCT/US2005/006334 filed on Feb. 25, 2005 (Lee-Sepsick et al.—inventors; Femasys Inc.—Applicant) (20 pages).
Communication pursuant to Article 94(3) issued Jul. 8, 2011 for European Patent Application No. 05723981.3, which claims priority to PCT/US2005/006334 filed on Feb. 25, 2005 (Lee-Sepsick et al.—inventors; Femasys Inc.—Applicant) (5 pages).
Response filed Sep. 2, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (3 pages).
Response filed Jul. 12, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (11 pages).
Response filed Apr. 13, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (1 page).

(56) References Cited

OTHER PUBLICATIONS

Response filed Apr. 5, 2011 for Indian Application No. 2536/KOLNP/2006, which claims priority to PCT/US2005/006334 filed on Feb. 25, 2005 (Lee-Sepsick et al.—inventors; Femasys Inc.—Applicant) (9 pages).
Office Action issued Apr. 21, 2010 for Indian Application No. 2536/KOLNP/2006, which claims priority to PCT/US2005/006334 filed on Feb. 25, 2005 (Lee-Sepsick et al.—inventors; Femasys Inc.—Applicant) (2 pages).
Certificate of Patent issued May 27, 2011 for Japanese Application No. JP2007-500782, which claims priority to PCT/US2005/006334 filed on Feb. 25, 2005 (Lee-Sepsick et al.—inventors; Femasys Inc.—Applicant) (2 pages).
Decision to Grant issued Apr. 19, 2011 for Japanese Application No. JP2007-500782, which claims priority to PCT/US2005/006334 filed on Feb. 25, 2005 (Lee-Sepsick et al.—inventors; Femasys Inc.—Applicant) (1 page).
Response to Office Action filed Nov. 4, 2010 for Japanese Application No. JP2007-500782, which claims priority to PCT/US2005/006334 filed on Feb. 25, 2005 (Lee-Sepsick et al. listed as inventors and Femasys Inc. listed as Applicant).
Office Action issued May 11, 2010 for Japanese Application No. JP2007-500782, which claims priority to PCT/US2005/006334 filed on Feb. 25, 2005 (Lee-Sepsick et al. listed as inventors and Femasys Inc. listed as Applicant).
International Search Report issued Sep. 22, 2005 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant) (8 pages).
Written Opinion issued Sep. 22, 2005 for PCT Application No. PCT/US2005/006334 filed on Feb. 25, 2005 which published as WO/2005/082299 on Sep. 9, 2005 (Lee-Sepsick et al. listed as inventors and Femasys Inc. listed as Applicant) (4 pages).
International Preliminary Report on Patentability issued Aug. 30, 2006 for PCT Application No. PCT/US2005/006334 filed on Feb. 25, 2005 which published as WO/2005/082299 on Sep. 9, 2005 (Lee-Sepsick et al. listed as inventors and Femasys Inc. listed as Applicant) (5 pages).

\* cited by examiner

METHODS AND DEVICES FOR DELIVERING TO CONDUIT

CROSS-REFERENCE TO RELATED APPLICATIONS

The present application claims the priority of U.S. Patent Application No. 61/703,002 filed Sep. 19, 2012; and is a continuation-in-part of U.S. patent application Ser. No. 13/684,549 filed Nov. 25, 2012, which is a continuation of U.S. patent application Ser. No. 13/286,127 filed Oct. 31, 2011 (now U.S. Pat. No. 8,324,193), which is a divisional of U.S. patent application Ser. No. 12/240,791 filed Sep. 29, 2008 (now U.S. Pat. No. 8,052,669), which is a continuation-in-part of U.S. patent application Ser. No. 11/065,886 (now U.S. Pat. No. 8,048,086) filed Feb. 24, 2005, which claims the priority of U.S. Provisional Patent Application No. 60/587,604 filed Jul. 13, 2004 and of U.S. Provisional Patent Application No. 60/547,491 filed Feb. 25, 2004; and is a continuation-in-part of U.S. patent application Ser. No. 13/684,546 filed Nov. 25, 2012, which is a continuation of U.S. patent application Ser. No. 13/285,908 filed Oct. 31, 2011 (now U.S. Pat. No. 8,336,552), which is a continuation of U.S. patent application Ser. No. 12/240,738 filed Sep. 29, 2008 (now U.S. Pat. No. 8,048,101), which is a continuation-in-part of U.S. patent application Ser. No. 11/065,886 filed Feb. 24, 2005 (now U.S. Pat. No. 8,048,086), which claims the priority of U.S. Provisional Patent Application No. 60/587,604 filed Jul. 13, 2004 and of U.S. Provisional Patent Application No. 60/547,491 filed Feb. 25, 2004; and is a continuation-in-part of U.S. patent application Ser. No. 13/684,529 filed Nov. 24, 2012, which is a continuation of U.S. patent application Ser. No. 13/285,744 filed Oct. 31, 2011 (now U.S. Pat. No. 8,316,854), which is a continuation of U.S. patent application Ser. No. 11/065,886 filed Feb. 24, 2005 (now U.S. Pat. No. 8,048,086), which claims the priority of U.S. Provisional Patent Application No. 60/587,604 filed Jul. 13, 2004 and of U.S. Provisional Patent Application No. 60/547,491 filed Feb. 25, 2004; and is a continuation-in-part of U.S. patent application Ser. No. 13/684,524 filed Nov. 24, 2012, which is a continuation of U.S. patent application Ser. No. 12/504,912 filed Jul. 17, 2009 (now U.S. Pat. No. 8,316,853), which is a divisional of U.S. patent application Ser. No. 11/065,886 filed Feb. 24, 2005 (now U.S. Pat. No. 8,048,086), which claims the priority of U.S. Provisional Patent Application No. 60/587,604 filed Jul. 13, 2004 and of U.S. Provisional Patent Application No. 60/547,491 filed Feb. 25, 2004; each of these applications is incorporated herein by reference in its entirety.

TECHNICAL FIELD

The present invention relates to methods and devices for delivering to conduits. In particular, the present invention is directed to methods and devices for delivery of fluid compositions to a conduit.

BACKGROUND OF THE INVENTION

In the medical and research fields, there are many clinical situations where it is desired or necessary to deliver or transfer substances within a body tube or conduit by using a device. It is often desirable for treatment or diagnostic purposes. Unfortunately, many delivery techniques are challenging or not optimal to achieve the desired therapeutic treatment or diagnostic evaluation.

What is needed are devices that deliver therapeutic treatments or can be used for diagnostic evaluations.

SUMMARY

The present invention comprises methods, systems, and devices for the delivery of therapeutic and/or diagnostic compositions to conduits. In particular, the present invention comprises methods, systems, and devices for the delivery of composition, for example delivery primarily at the cornua of the fallopian tube(s), and a composition may move to, into and/or through the tube to the ovaries and to the peritoneal cavity. The devices of the present invention may be used to deliver compositions comprising sonographically or fluoroscopically visible materials to evaluate the condition of the conduit, such as in diagnosis of the state of a fallopian tube. A conduit may be a naturally occurring conduit such as a tube or vessel in the body or may be a conduit that has been introduced in the body such as a medical device or through surgical means.

The present invention also comprises delivery systems, methods, and devices for the delivery of therapeutic compositions to one or more fallopian tubes to enhance fertility, such as for artificial insemination or ovulation stimulation, to treat tubal disorders, such as ectopic pregnancy, treat infections, such as pelvic inflammatory disease, or treat cancer near, in, around, at the cornua or fimbriae exit of the tube.

An aspect of the present invention is a method that comprises introduction of a delivery device system for delivery of one or more compositions to one fallopian tube at a time, in a sequential manner, or to both fallopian tubes sequentially or simultaneously without the necessity to remove, reinsert, or substantially reposition the delivery device. Such a device may be sized for each recipient by visualization of the anatomy of the recipient before use of the device in the recipient. A composition may be delivered for diagnosis followed by a composition for treatment or a composition for treatment alone may be provided. The composition may be delivered in single dose or in a delivery vehicle to allow for controlled, extended or sustained release of the composition. A composition can be used alone or combined with other compositions and can be delivered prior, during or after other procedures.

DETAILED DESCRIPTION

Figure 1:
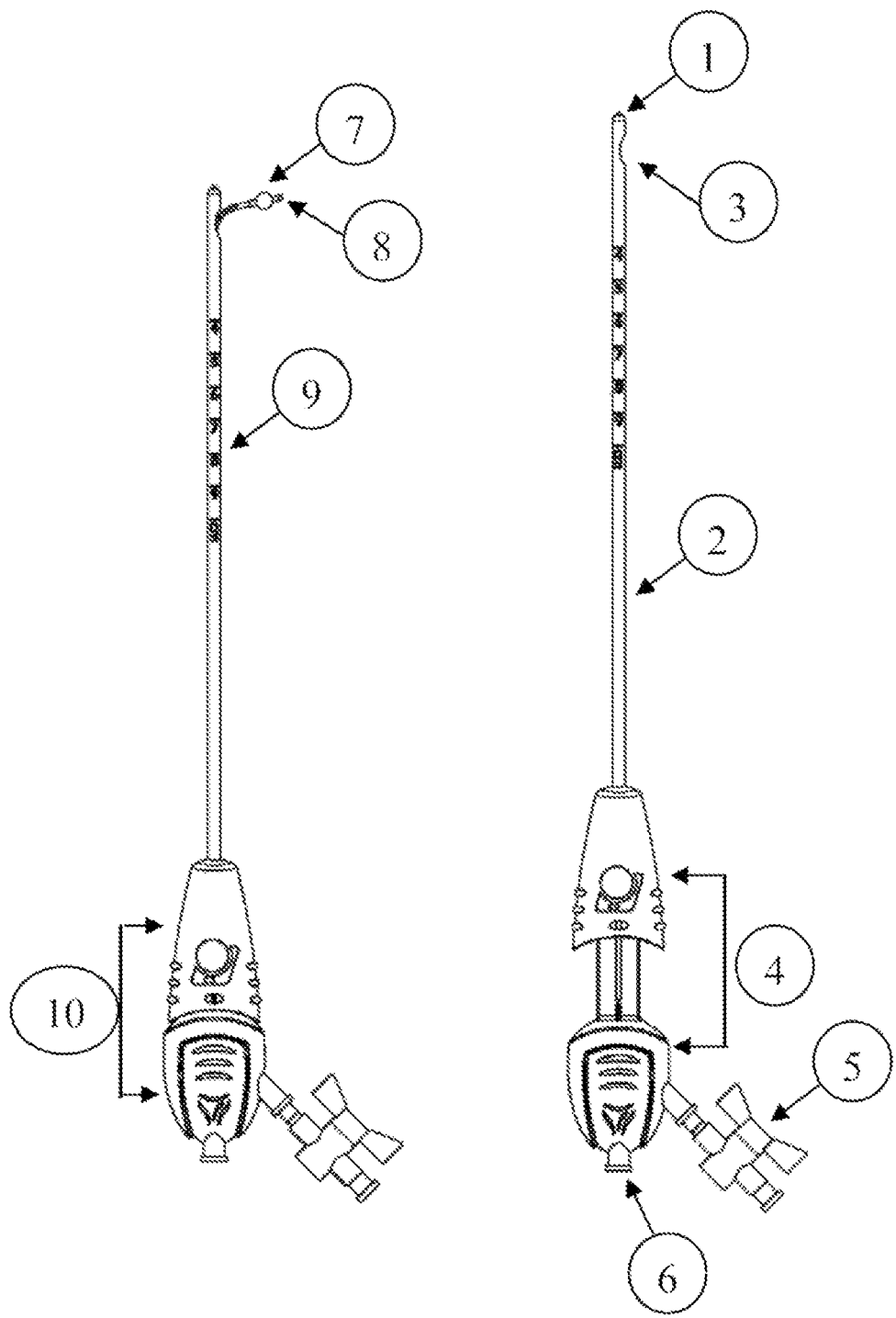
FIG. 1 shows an embodiment of a delivery device with one exit port and one catheter for the transcervical delivery of compositions.

The present invention comprises delivery systems, methods and devices for delivering one or more compositions to conduits. The present invention comprises delivery systems and methods for diagnosing or treating conduits in the body through the placement of diagnostic or therapeutic material (compositions) using a delivery device. One aspect of the present invention comprises treating conduits. In another aspect, the present invention comprises diagnosing conduits followed by treatment. Yet another aspect of the present invention comprises methods, delivery systems and compositions to diagnose or treat the fallopian tube(s) of a female mammal, and methods and systems to treat physical structures reached by passage through the fallopian tube(s). Methods, systems and compositions of the present invention may be used in embodiments that permit non-surgical, office-based procedures.

The present invention comprises methods for diagnosing or treating conduits, particularly conduits found in human or other animal bodies. Such conduits may exist naturally in the body or be present because of disease, damage, placement of medical devices or surgical means.

A method of the present invention comprises use of devices disclosed herein is to deliver compositions to a structure. The delivery of occlusive compositions or those to re-open an occluded conduit are disclosed in U.S. Pat. Nos. 8,048,086; 8,048,101; 8,052,669 and related, continuing applications including U.S. patent application Ser. Nos. 12/504,912; 13/285,744; 13/285,908; and 13/286,127, each of which are herein incorporated in its entirety. Therapeutic or diagnostic treatments may be provided to humans or animals by delivering therapeutic compositions comprising therapeutic agents or diagnostic compositions, such as contrast media compositions to a structure by using the delivery device and catheter assembly as described herein. For example diagnostic compositions may be provided to a fallopian tube or both fallopian tubes to evaluate the condition of the tube, such as tubal occlusion, tubal patency, hydrosalpinx, or pyosalpinx. Diagnostic compositions comprise compounds, such as radiopaque dye, saline and air contrast, saline to evaluate by imaging, such as, fluoroscopically or sonographically.

For example, therapeutic compositions may be provided to a fallopian tube or both fallopian tubes to enhance fertility. Therapeutic compositions comprise sperm, which can be processed or washed, hormones for fertility, fertility enhancing compounds, gametes, ova, combinations of sperm and ova, one or more zygotes, or one or more embryos, gamete and embryo deposition, ovarian stimulating compounds or gonadotropins (i.e., Follistim, Gonal-F, Repronex, Menopur, Bravelle, letrozole), ovulation induction compounds (I.e., Clomiphene citrate, such as Clomid or Serophene), oviductal glycoproteins, compounds to reduce the likelihood of implantation failure (fertilized egg) or miscarriage (i.e., granulocyte colony stimulating factor, additives from the group consisting of cytokines that suppress TH1 immune response, enhance TH2 immune response, anti-inflammatory agents, inhibitors of pro-inflammatory cytokines), hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds or combinations thereof.

For example, therapeutic compositions may be provided to a fallopian tube or both fallopian tubes to treat disorders, infections or cancer near, in, around, at the cornua or fimbriae exit of the tube, such as for treating ectopic pregnancy, salpingitis (i.e., pelvic inflammatory disease), tubal spasm, tubal occlusion (i.e., providing shockwaves, chemical means including solvents, biological means including enzymes, or mechanical means including stiff or cutting catheter ends), tubal obstruction, tubal obliteration (i.e., silver nitrate), tubal disease, manage tubal condition pre, during or post treatment, tubo-ovarian abscess, paratubal cysts, ovarian cysts, benign tubal tumors, benign ovarian tumors, tubal cancer, ovarian cancer, prophylactic treatment of tube or ovaries. Therapeutic compositions comprise compounds to treat ectopic pregnancies (i.e., methotrexate, PGF2a, or hypertonic glucose solution), compounds to treat fallopian tube occlusions (i.e., Ringer's lactate solution, Solu-Cortef, heparin to cleanse and maintain fallopian tube patency), compounds for pain management (i.e., lidocaine, lignocaine, bupivacaine, mepivacaine), antibiotics (i.e., Doxycycline), narcotics, medications, hydrocortisone, anti-inflammatory, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, compounds for cancer or anti-cancer drugs (i.e., paclitaxel, cisplatin, platinum-taxane, carboplatin, cyclophosphamide, docetaxel), other compounds that may treat or prevent conditions related to the fallopian tube, uterus, ovaries, peritoneum, or other organs or coverings reached by a composition flowing from the cornua or ostia of a fallopian tube or combinations thereof.

Compositions used as described herein with devices of the present invention can be incorporated in a carrier, depot, injectable, capsule, particles, vessel, gels, fibers, or equivalent means for immediate, controlled, extended or sustained release of one or more compositions. Compositions may display a narrower therapeutic range, where controlling the release of the compound is necessary to effectively treat. For example, extending the release of a compound may be achieved through the manipulation of physiochemical properties, the use of formulation technologies such as microspheres and nanospheres, and balancing the in vivo properties of the compound (such as half-life). Post-procedure methods and compositions may further comprise the use of hormonal agents to prohibit menstrual shedding of the endometrium is also contemplated to minimize the risk of expulsion for a period of time, for example to allow for a period of time for resorption of the composition. For example, use of a long-acting hormonal medication such as an injectable medroxyprogesterone acetate depot may serve the function of both the pre- and post-operative hormonal therapy without the need for reliance on patient compliance. Post-operative methods and compositions may further comprise antibiotic or steroidal compositions.

In methods where delivery of such therapeutic or diagnostic compositions are provided by directly providing such compositions to structures, the compositions may further comprise multiple steps of delivery with delivery of a diagnostic compound initially, followed by a therapeutic composition, and the delivery of the diagnostic or therapeutic compositions may be monitored, viewed or assisted by techniques such as ultrasound. A composition comprising therapeutic agents or diagnostic compounds may be provided as one composition or may be sequentially provided in separate compositions using a delivery device of the present invention and may provide both treatment and diagnosis of the condition of a structure in one step or multiple steps of delivering the composition. Alternatively, the sole or combined therapeutic agent composition may be delivered to limit or locate the medicament in the targeted structure with or without the support of imaging allowing for treatment to occur with or without diagnosis sequentially or simultaneously.

A method of the present invention comprises delivering to a body tube, such as a fallopian tube, living cells or tissues, for example, for artificial insemination. Artificial insemination has been used in clinical medicine for more than 200 years through a variety of different techniques for the treatment of infertile couples. The original technique used for over a century was intravaginal insemination, where a semen sample was placed high in the vagina. Techniques then progressed to include intracervical insemination where semen was placed into the endocervix or endocervical canal. In the 1960s, a major breakthrough came when methods were developed for purifying sperm samples and for placement within the uterus, termed intrauterine insemination (IUI). The rationale for performing IUI is that it increases the number of motile spermatozoa at the site of fertilization by placing directly in the uterus at the time of ovulation with a catheter. Bypassing the cervix, which also acts as a reservoir and a barrier for sperm, brings the spermatozoa closer to the released oocyte. Since conception occurs in the fallopian tube, direct tubal catheterization has been utilized for injection of spermatozoa, either by laparoscopy or transvaginally by ultrasound guidance or by tactile sensation, also termed intratubal insemination. Since this method is technically challenging, it has been performed by an infertility specialist with the appropriate skill set. Another technique involves the use of intrauterine catheters or devices placed into the uterine cavity, similar to those used for hysterosalpinography, which forces the passage of sperm through the fallopian tubes once pressure has increased in the uterine cavity. Depending on the device configuration, prevention of inseminate reflux from the cervix can also be accomplished, either by a fixture on the catheter (i.e., balloon at the cervix) or specialized speculum that clamps the cervix and cervical canal. Direct passage through the fallopian tubes, bypassing possible obstacles in the fallopian tubes from membranes to mucus, of the prepared sperm increases the density of capacitated spermatozoids near the oocyte and the intra-peritoneal cavity and may positively impact the pregnancy success rate. Fallopian tube sperm perfusion and intrauterine tuboperitoneal insemination are other terms used to describe the same method of filling the uterine cavity followed by passage through the interstitial part of the tubes and the ampulla, finally reaching the peritoneal cavity and pouch of Douglas, where the inseminate would be mixed with the peritoneal and follicular fluids. Results of such techniques have varied and are attributed to the wide range of different instruments used to facilitate the method. It has been reported that preventing leakage of inseminate leading to a higher fallopian sperm perfusion provides results twice as promising as standard IUI. The devices described herein allow for the effect of directed delivery of the sperm to the fallopian tube(s) but without the skill and equipment required for direct cannualization or the need to fill the entire uterine cavity to force delivery into the tubes, which will ensure that performance of the treatment can be performed by a general physician (i.e., gynecologist) as well as a specialist. In contrast to the devices that deliver sperm into the uterine cavity, the amount of sperm required by the devices described herein is considerably less as the delivery is directly to the opening of the fallopian tube(s).

A method of the present invention comprises use of a device of the present invention for delivery to a body tube for the selective delivery of ovulation stimulating hormones to induce ovulation, which is necessary for pregnancy. Therapeutic compositions to stimulate the ovaries to produce multiple eggs, include but are not limited to, follicle stimulating hormones (FSH), such as Follistim, Gonal-F, Repronex, Menopur and Bravelle, which can be given to prior to an assisted reproduction procedure, such as In Vitro Fertilization (IVF). For the treatment of ovulation dysfunction, therapeutic compositions include Clomiphene citrate, such as Clomid or Serophene, which can restore normal ovulation in about 80% of the patients whose only factor is ovulatory dysfunction. There is an increased incidence of multiple births by these methods. The devices described herein would allow for the direct delivery to and through the fallopian tube(s) to the ovaries to stimulate and induce ovulation, in a single application or in a few applications, as opposed to multiple injections. Further, providing an overall lower amount of a therapeutic compound may reduce the likelihood of ovarian hyperstimulation syndrome, a potentially life threatening complication resulting from overstimulation of the ovaries, requiring hospitalization and aggressive treatment.

A method of the present invention comprises use of a device of the present invention for delivery to a body tube for the diagnosis and treatment of an ectopic pregnancy. The incidence of ectopic pregnancy has significantly increased over the past two decades but the mortality rate has decreased, likely due to better awareness. Ectopic pregnancy results from a delay in the passage of the fertilized ovum through the fallopian tube, with the ectopic occurring in the tube located at its distal parts, particularly in the ampulla section. Diagnosis of an early ectopic pregnancy has been accomplished by determining by the rate of fluoroscopic imaging of an ampullary radiolucency upon injection of contrast material through a selective salpingography catheter. The devices described herein can achieve evaluation by allowing delivery of diagnostic compounds that are visible by fluoroscopy or sonography to one or both fallopian tubes at a time. Medical therapy may be systemic where an intramuscular dose of methotrexate is given over days or local delivery into the affected tube with a single-dose of methotrexate (or an equivalent therapeutic compound). Treatment can be at the same time or at a later time from the diagnostic evaluation. Methods that have been used to deliver methotrexate to the fallopian tube include selective salpingography under fluoroscopy, transcervical tubal catheterization/cannualization, ultrasound guided local injection, laparoscopic salpingotomy, and transvaginal injection under sonographic control. All methods were deemed feasible but those not requiring laparoscopy or operative intervention bear a lower cost as a less invasive approach. The devices described herein eliminate the need for laparoscopy or cannualization of the fallopian tube, greatly simplifying the procedure.

A method of the present invention comprises use of a device of the present invention for directed delivery to a body tube for delivery of drugs for cancer treatment of the fallopian tubes or ovaries. Fallopian tube cancer is very rare and its symptoms can resemble other problems which makes diagnosis difficult. There is evidence to suggest that the fallopian tube could be the source of ovarian cancer. Since the ovaries and tubes are closely related to each other, it is thought that these fallopian cancer cells can mimic ovarian cancer. Ovarian cancer is the second most common gynecologic cancer and the deadliest in terms of absolute numbers. In addition to local therapy and systemic chemotherapy, intraperitoneal chemotherapy is employed, where the drug is given directly into the abdomen and pelvis through a tube inserted into the abdomen. Although clinical studies have demonstrated that there is a 25 percent reduction in the risk of death with intraperitoneal treatment in comparison to the intravenous therapy group, reduced quality of life during the treatment was noted to affect the likelihood of the patient enduring all planned intraperitoneal doses. Many complications and patient discomfort/pain have been noted directly related to the access device through the abdomen and abdominal pain during infusion. In addition, to remove the intraperitoneal catheter once treatment is complete or not deemed necessary, the woman must undergo minor surgery under local anesthesia to open the previous incision down to the port, cut and remove the device. The devices described herein would allow for delivery of the drug to and through the fallopian tube to the ovaries and peritoneal cavity in a much less invasive technique and can be performed repeatedly without leaving the device in place. The methods described would provide for the effect of intraperitoneal delivery, however, transcervically by providing the drug from within the uterine cavity as opposed to the peritoneum. This will increase compliance and possibly improve outcomes.

A method of the present invention comprises use of a device of the present invention for directed delivery to a body tube for delivery of medications for tubal disease, infections, or for the management of pain. Women with the clinical diagnosis of pelvic inflammatory disease (PID) were to be evaluated by laparoscopy would usually have visual evidence of acute tubal inflammation, therefore, the clinical diagnosis of PID has been argued to represent women with visually confirmed acute salpingitis. Salpingitis is an infection and inflammation in the fallopian tubes that usually has its origin in the vagina and ascends to the fallopian tube, affecting both tubes typically by spreading of the infection via the lymph vessels. Salpingitis can lead to formation of scar tissue, which may block the tubes completely leading to infertility or partially increasing the risk of an ectopic pregnancy. Diagnosis of acute PID is usually based on clinical criteria and can be challenging for even the most astute clinicians. An approach to its diagnosis includes the need to intervene with antimicrobial therapy early on the course of this ascending infection. The CDC recommends Doxycycline be administered for treatment orally or intravenously, which when administered by these methods may lead to esophageal ulcers, gastrointestinal irritation, and local inflammation, which may lead to premature cessation of treatment. Drug delivery has successfully been accomplished transcervically with Doxycycline encapsulated in nanoparticles made of biodegradable chitosan to improve sustained delivery of the drug, minimize adverse effects and improve drug efficacy. With the devices described herein, greater emphasis of delivery to the fallopian tube(s) can be accomplished. For the management of pain, pre, during or post procedure, transcervically delivered analgesia has been found to be more effective than that administered topically, leading to quicker time to discharge and less pain.

As used herein, the term "conduit" shall refer to any tube, duct, or passage, whether natural or synthetic, which carries gas, fluids or solids in a biological system.

As used herein, "diagnose" refers to evaluating with imaging the transport of gas, fluids, or solids to and through a conduit. As used herein, "diagnostic material" refers to a composition that is capable of being imaged in a conduit once delivered or during delivery. As used herein, diagnostic material means the initial composition that is placed or inserted into the conduit, as well as the composition, whether the physical, biological, or chemical nature of the composition has changed or not, that is in place in the conduit and provides for the evaluation of the conduit or flow through the conduit for evaluation. The meaning of the term can be determined from its use in the sentence. Diagnostic compositions, diagnostic compounds, and diagnostic materials are terms used interchangeably herein.

As used herein, diagnostic material comprises any synthetic or natural compositions or any combination of synthetic and natural compositions that can be placed at the desired site in the conduit using the delivery systems of the present invention. Diagnostic materials of the present invention may comprise materials that are fluid, fluid and gas, gas, semi-solid, gels, solids, and combinations thereof. The diagnostic materials may further comprise a pre-formed material that is of a shape or size that travels to the conduit. Disclosed herein are exemplary compositions and materials suitable for use as diagnostic compositions.

As used herein, "therapeutic" refers to treating without or with imaging assistance the transport of gas, fluids, or solids to and through a conduit. As used herein, "therapeutic material" refers to a composition that is capable of being imaged if imaging assistance is used in a conduit once delivered or during delivery. As used herein, therapeutic material means the initial composition that is placed or inserted into the conduit, as well as the composition, whether the physical, biological, or chemical nature of the composition has changed or not, that is in place in the conduit and provides for the treatment of the conduit or areas beyond the conduit. The meaning of the term can be determined from its use in the sentence. Therapeutic compositions, therapeutic compounds, and therapeutic materials are terms used interchangeably herein.

As used herein, therapeutic material comprises any synthetic or natural compositions or any combination of synthetic or natural compositions that can be delivered to the desired site in or around the conduit using the delivery systems of the present invention. Therapeutic materials of the present invention may comprise materials that are fluid, semi-solid, gels, solids, and combinations thereof. The therapeutic materials may further comprise a pre-formed material that is of a shape or size that travels to or out of the conduit. Therapeutic compositions may further comprise combinations of two or more of any of the therapeutic materials. Disclosed herein are exemplary compositions and materials suitable for use as therapeutic compositions.

As used herein, non-invasive visualization or imaging refers to all forms of imaging. Examples of non-invasive imaging include all forms of ultrasound, fluoroscopy, or magnetic resonance imaging, which are incorporated within the scope of this definition.

As used herein, the term "delivery system" comprises all components necessary to deliver a diagnostic or therapeutic material, and may comprise an introducer, delivery device or catheter(s), combinations thereof, and any other components necessary for the full functioning of the delivery system.

In general, the methods of the present invention comprise administration of delivery systems that deliver compositions that are capable of diagnosing or treating conduits. The delivery systems comprise devices that are capable of delivering diagnostic or therapeutic compositions to the desired site. Disclosed herein are exemplary methods, delivery systems, and compositions for diagnosis or treatment of conduits of the reproductive tracts of mammals. Such methods and compositions can be used in other physiological systems and biological sites of humans or other animals, and delivery systems for such biological sites are contemplated by the present invention.

One aspect of the present invention comprises methods of diagnosis with imaging visualization or treatment with or without imaging visualization for mammalian females of a delivery system that delivers a diagnostic or therapeutic composition to a target site, for example, from the cornual aspect of the uterus into each fallopian tube, wherein the composition is capable of diagnosing or treating each fallopian tube.

The method comprises introduction of the device, including inserting the shaft of the introducer through the cervix until the atraumatic tip contacts the uterine fundus as determined by non-invasive visualization such as ultrasound or through the sensation of the operator. When the tip is appropriately placed, optionally, the operator may engage a guide that aids in confirming delivery device placement. For example, this guide may be a depth stop, a member which indicates that the tip is in position and the introducer shaft should be not be introduced any further. With the introducer in position, one or two double-lumen balloon catheters is advanced from the exit port of the introducer channel until it exits the channel in the shaft of the introducer, and the tip of the catheter is located within the uterine cornua.

A further aspect of the present invention comprises methods wherein each catheter undergoes the following steps. At a proximal end of the catheter, one end of the catheter which is near the handle and distant from the delivery end of the catheter, a cartridge containing balloon distension medium is connected to the balloon fitting, the stopcock is opened, and the distension medium is delivered to effect inflation of the balloon positioned at the delivery end of the catheter. The stopcock is then closed and the cartridge is disconnected from the fitting. At a proximal end of the delivery device, a cartridge containing the diagnostic or therapeutic composition is then connected to luer, the material is delivered through the catheter and out of the delivery end of the catheter that is at or adjacent to the delivery site. The material may be delivered directly to the target site or may move from the delivery site to the target site location. Once the material has been delivered, the balloon is deflated or the inflated balloon can be held in position to ensure forward flow of material, for example, once a tubal spasm has subsided. Each catheter is retracted until it is housed within the introducer shaft or fully removed from the introducer. If necessary, the guide is disengaged. The delivery system is then withdrawn from the patient. The diagnostic or therapeutic material may be delivered sequentially or simultaneously to the two fallopian tubes. The device is designed for delivery of compositions to two separate sites with minimal to no repositioning and without removal of the device, including the introducer, until the procedure is complete. One or both of the delivery catheters may be retracted into the introducer without removal of the entire device.

Yet another aspect of the present invention comprises a delivery system for delivery of a composition into the fallopian tubes comprising a delivery device comprising an introducer with two channels, a housing means which may function as a handle if needed, means for attachment of one or more containers of balloon distension medium and the composition, and two catheters for delivery of the composition. The catheters may comprise an end structure, which is a balloon or other similarly functioning member that may hold the catheter in position, prevents leakage of the material from the target site or performs both functions. The composition may be delivered from the container through the catheters to one or more target sites.

One aspect of the present invention comprises a delivery system comprising an introducer, one or more catheters wherein each may have a distinct function or design, and one or more cartridge components wherein each cartridge may have a distinct design and contain a distinct material.

Now referring to FIG. 1, an exemplary embodiment of a delivery device is shown comprising the following subcomponents: an introducer with a tip (1) which is shaped for atraumatic insertion through the cervix; the introducer shaft (2), generally a structure which may be cylindrical in nature, which contains one catheter channel, which runs the interior length of the shaft and has an opening for exit of a catheter from the shaft (3); catheter features a pre-formed curve designed to aid in movement of the delivery end of the catheter from the introducer shaft into the cornual aspect of the uterus, and includes two lumens, one for inflation and deflation of the balloon that at its proximal end has a stopcock (5) and one for delivery of the material that at its proximal end has a luer fitting (6); and an opened handle (4) which has an ergonomic design for gripping by the operator, retracts the catheter into the shaft. The catheter can be extended from the shaft by closing the handle (10), exposing the balloon (7), which when inflated may hold the catheter in place and prevent leakage of the material away from the target and has a tip (8) through which the compositions exit to be delivered to the target site. The guide (9) for the delivery device shown in this example is depth markings.

Figure 2:
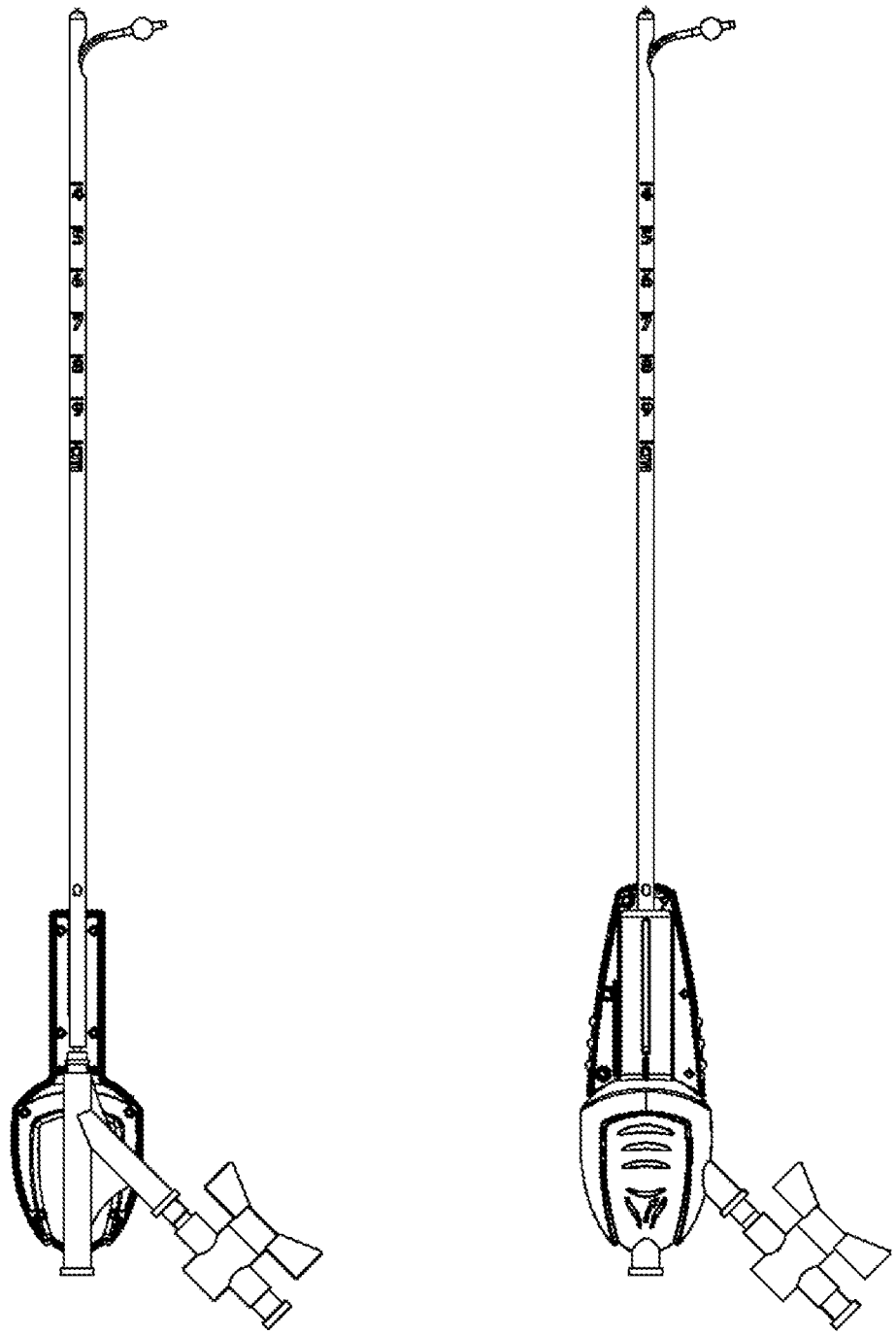
FIG. 2 shows an internal view of the delivery device from FIG. 1.
Figure 3:
FIG. 3 shows an embodiment of a delivery device with two exit ports and two catheters for the transcervical delivery of compositions.
Figure 4:
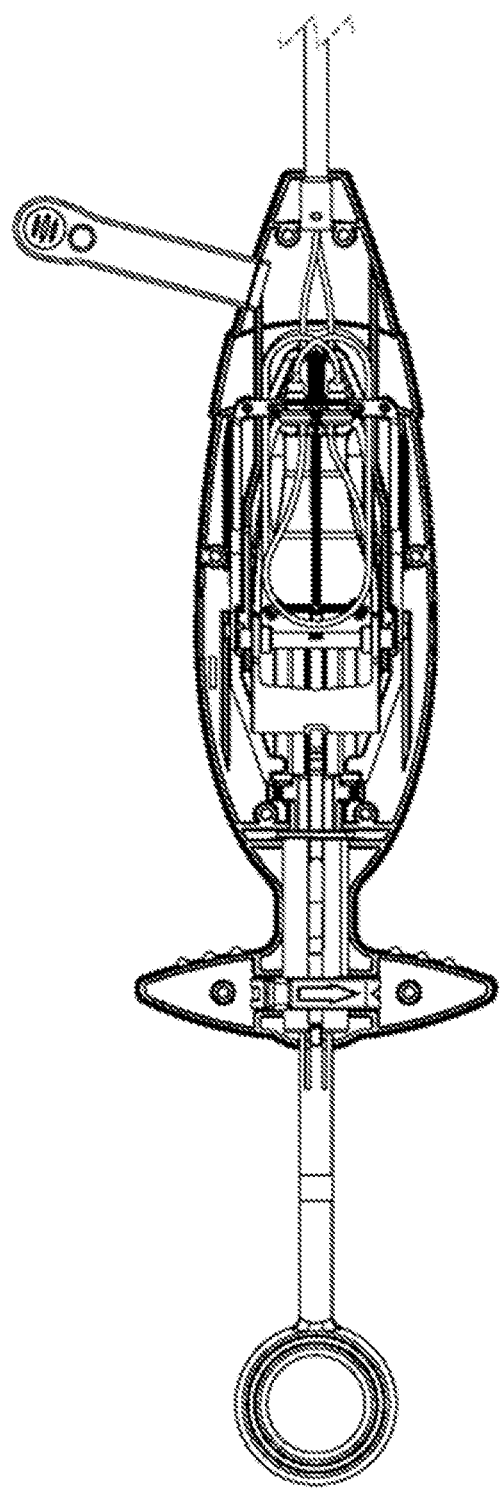
FIG. 4 shows an internal view of the delivery device from FIG. 3.
Figure 5:
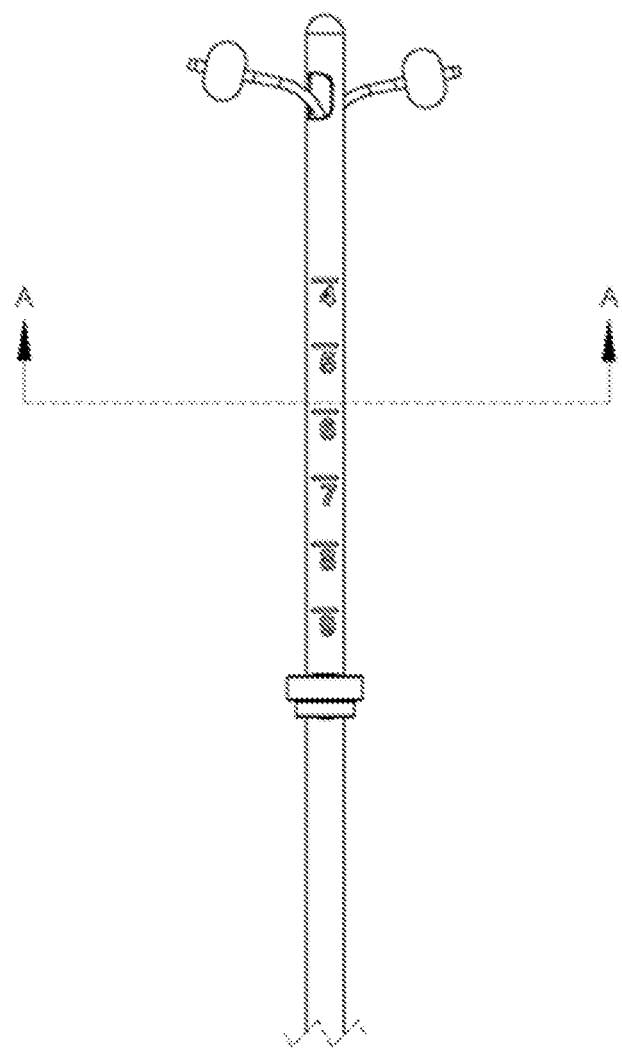
FIG. 5 shows an embodiment of a cross section view of the introducer shaft with multiple dual lumens, wherein the septum forming two lumens is constructed of a solid, rigid, semi-rigid, or flexible material

FIG. 2 shows internal aspects of the delivery device described herein.

The delivery systems of the present invention comprise means for introducing delivery devices into the body, means for providing diagnostic or therapeutic materials such as reservoirs and pumps, devices for in situ delivery of compositions comprising diagnostic or therapeutic materials; means for visualization of procedures, pre- and post-procedural compositions and methods of treatment.

As envisioned for delivery to a conduit, a delivery system comprises a transcervical introducer sheath generally made of a standard medical-grade metal or plastic such as stainless steel, nylon, PTFE, or polyurethane, which may be naturally sonolucent or may require enhancement of ultrasound visibility by coating with a sonolucent material or otherwise modifying the material. The sheath may comprise an atraumatic tip to allow for comfortable placement and, combined with selection of a suitably flexible material, to prevent damage to the uterine wall. The introducer shaft has sufficient diameter to allow for introduction of other components of the delivery system. The introducer may contain one, two or more channels that guide catheters into position, for example delivery catheters for delivery of materials. The introducer may include a mechanism to modify the angle of the introducer relative to the surrounding tissues, such as the cervix or uterus, to allow for a better fit to the anatomy of the individual patient, including such individual variations as ante- or retroverted/ante- or retroflexed uterus. Modified versions of the introducer may allow for uses other than for the diagnosis or treatment of the fallopian tube(s), such as the localized delivery of contrast media for confirmation of tubal patency or the delivery of therapeutic compounds to the fallopian tube(s) or devices for diagnosis, treatment, or examination of the tube, including the delivery of systems for treating fertility, ectopic pregnancies, infection or cancer. One aspect of the introducer sheath is that it can be visualized using noninvasive techniques such as ultrasound. Visualization may be used to guide accurate placement and to ensure that the tip of the device does not penetrate the uterine wall. A delivery device stabilizer may be included to ensure that accurate placement is maintained throughout the procedure. The delivery device stabilizer may comprise or include a means to fix or hold the introducer in place, such as a mechanism or device to attach or hold the introducer within the cervix or to otherwise maintain the device in the desired position, minimizing risk to the patient and allowing the operator greater flexibility to carry out other aspects of the procedure. Fixation may be accomplished through physical means such as clamping, suction, wedging, inflation, or by other means that maintain the device in the desired position.

A delivery system of the present invention comprises a device that can be configured in a collapsed, retracted, or folded form for insertion through the cervix, which may comprise an introducer sheath. After introduction, the device is positioned allowing an atraumatic tip containing a single or multiple holes at the tip of the device to reach the desired location, such as within the cornual aspect of the uterus at or near the ostium of a fallopian tube. The present invention comprises a device that has at least one end of a delivery catheter with an opening that is placed within the cornual aspect of the uterus at or near the ostium of a fallopian tube. In one embodiment, the delivery device comprises two delivery catheters, with each catheter having its delivery opening positioned simultaneously or sequentially at the ostia of both fallopian tubes. In another embodiment, such a device may be shaped like a Y, a T, or an arrow wherein the two delivery ends of the shape are positioned within the uterine cornua at or near the ostia. The delivery system may utilize existing catheter-based technology, for example, balloon catheters, and may incorporate standard materials such as Pebax, nylon, PTFE, polyurethane, vinyl, polyethylene, ionomer, polyamide, polyethylene terephthalate, and other materials. These materials may be naturally sonolucent or may be modified to enhance their ultrasound visibility, such as by coating or the inclusion of air bubbles within the material. Embodiments of the present invention may include a means for controlled flexion or rotation of the delivery system, which may aid in positioning one or more ends at the desired anatomic location. The catheters may be designed with one or more curves that ensure that the tip is guided to the uterine cornua. Such curves may be either pre-formed to suit a majority of female reproductive anatomies or may be selected based on the individual anatomy of a single female patient.

The present invention comprises methods for diagnosis or treatment of fallopian tubes comprising delivery of devices, such that the methods incorporate intra-procedure non-invasive visualization without hysteroscopy, and positioning of the delivery ends of a delivery device within the uterine cornua at or near the ostia of both fallopian tubes without the need for removal and reintroduction of instrumentation. Embodiments of the present invention comprise delivery devices that are sized appropriately for a general population of patients and also comprise delivery devices that are custom-fitted and individually tailored to meet individual patient anatomical needs. Delivery devices taught in the prior art, such as U.S. Pat. Nos. 5,746,769; 6,145,505; 6,176,240; 6,476,070; 6,538,026; 6,634,361; 6,679,266; and 6,684,384; 5,954,715; 6,068,626; 6,309,384; 6,346,102; and 6,526,979 do not consider individual patient anatomy, may require the use of a hysteroscope for direct visualization, and necessitate cannulation of each tube sequentially, with the need to reposition, withdraw and reinsert the device, enhancing the technical difficulty of the procedure and consequently the inherent risk of failure.

One aspect of this invention contemplates the use of pre-procedure imaging, such as by ultrasound, to allow for selection or adjustment of lengths and angles of the deployed delivery device and selection of appropriate delivery device stabilizer to accommodate individual patient anatomy. This pre-procedure imaging is used to rule out anomalies that may preclude use of the system and may be used to determine the uterine width between the fallopian tubes to select the correct size delivery system or to adjust the angle or shape of each of the two delivery ends such that each would be properly located within the uterine cornua at or near the ostium of a tube on deployment. Imaging may also elucidate the size and shape of the cervical os and canal, guiding selection of size and shape of delivery device stabilizer or spacer. Alternatively, one of a set of predetermined sizes of the delivery system could be selected based on the pre-procedure imaging information. The ability to adjust placement of the delivery ends or tips, including the angle and length for each individual end or in combination, during the procedure based on tactile feedback, imaging, or both tactile and imaging information is also contemplated.

Methods of the present invention comprise visualization of one or more steps of the methods. Visualization of the insertion, placement of the device, and release of the composition are included in methods for providing the diagnostic or therapeutic material. Such visualization methods are known to those skilled in the art. U.S. Pat. Nos. 4,731,052 and 4,824,434 teach that ultrasound may be used for visualization of internal structures. The compositions and devices of the present invention comprise materials that allow for visualization, such as by ultrasound, during the procedure to ensure appropriate patient selection and device placement and localization, and for post-application monitoring to confirm appropriate material placement.

Once the delivery device is appropriately placed, the material is introduced through the delivery device to diagnose or treat the fallopian tubes. In one aspect of the invention, the delivery device has individual channels in the shaft of the introducer, with capability to provide a delivery end or tip directed toward the opening of a fallopian tube. An aspect of the invention allows for the simultaneous or sequential delivery of material to the fallopian tubes without the need to withdraw and reinsert or substantially reposition the device. The material is delivered by actions of the operator manually or automatically once the device is in position. One aspect of the invention contemplates the material is visualizable by non-invasive imaging such as ultrasound. Materials may be naturally sonolucent or may be modified to have enhanced sonolucency by the introduction of materials or bubbles such as microbubbles of air or gas. These microbubbles may be present within the material prior to attachment to the delivery system or may be introduced into the material during the delivery process, such as through the use of a cavitation mechanism.

Disclosed herein is a method for diagnosing and treating at least a portion of one or two conduits in a human or animal body, comprising, (a) providing a delivery system that delivers an effective amount of one or more compositions, wherein the delivery system comprises a delivery device comprising an introducer shaft comprising one or two exit ports for providing one or two catheters, one or two catheters each comprising an end structure on a delivery end, one or more compositions, and a means for providing the one or more compositions into and through the one or two catheters; (b) delivering an effective amount of a composition comprising a diagnostic material such that the composition enters at least a portion of the one or two conduits; and (c) delivering an effective amount of a composition comprising a therapeutic material such that the composition enters at least a portion of the one or two conduits.

In an aspect, the disclosed method can comprise diagnosing at least a portion of one or two conduits. In an aspect, one conduit can be diagnosed. In an aspect, two conduits can be diagnosed. In an aspect, diagnosing at least a portion of one or two conduits can comprise delivering an effective amount of the composition comprising a diagnostic material such that the material enters the lumen of the one or two conduits. In an aspect, the disclosed method can comprise treating at least a portion of one or two conduits. In an aspect, one conduit can be treated. In an aspect, two conduits can be treated. In an aspect, the method can comprise diagnosing at least one conduit following the treating of at least one conduit. In an aspect, one of the conduits can be a fallopian tube of a mammal. In an aspect, two of the conduits can be a fallopian tube of a mammal.

In an aspect of a method for diagnosing and treating at least a portion of one or two conduits in a human or animal body, delivering an effective amount of a composition comprising a diagnostic material and delivering an effective amount of a composition comprising a therapeutic material can occur without removal and re-introduction or substantial repositioning of the introducer shaft.

In an aspect of a method for diagnosing and treating at least a portion of one or two conduits in a human or animal body, delivering an effective amount of a composition comprising a diagnostic material and delivering an effective amount of a composition comprising a therapeutic material can occur sequentially or can occur simultaneously.

In an aspect of a method for diagnosing and treating at least a portion of one or two conduits in a human or animal body, a composition comprising a diagnostic material and the composition comprising a therapeutic material can be the same composition or can be different compositions.

In an aspect of a method for diagnosing and treating at least a portion of one or two conduits in a human or animal body, the introducer shaft can have one exit port and one catheter, and one or more compositions can be provided into and through the one catheter. In an aspect of a method for diagnosing and treating at least a portion of one or two conduits in a human or animal body, the introducer shaft can have two exit ports and two catheters, and one or more compositions can be provided into and through the two catheters.

In an aspect of a method for diagnosing and treating at least a portion of one or two conduits in a human or animal body, each of the one or two catheters can have an attachment means on a proximal end. In an aspect, each of the one or two catheters can be a dual lumen balloon catheter. In an aspect, both catheters can be a dual lumen balloon catheter. In an aspect, the end structure of each of the one or two catheters can maintain the delivery end in an uterine cornua and can aid in localized delivery of one or more compositions. In an aspect, the end structure of both catheters can maintain the delivery end in an uterine cornua and can aid in localized delivery of one or more compositions. In an aspect, the therapeutic material can be embodied within a carrier, depot, injectable, capsule, particles, vessel, gels, fibers, or equivalent means for immediate, controlled, extended, or sustained delivery. In an aspect, the delivery can be immediate. In an aspect, the delivery can be controlled. In an aspect, the delivery can be extended. In an aspect, the delivery can be sustained.

In an aspect of a method for diagnosing and treating at least a portion of one or two conduits in a human or animal body, the therapeutic material can enhance fertility. In an aspect, the therapeutic material that can enhance fertility can comprise sperm material or ovulation inducing or stimulating hormones. In an aspect, the ovulation inducing or stimulating hormones can comprise one or more of Follistim, Gonal-F, Repronex, Menopur, Bravelle, Clomid, Serophene. In an aspect, a combination of ovulation inducing or stimulation hormones can be used to enhance fertility.

In an aspect of a method for diagnosing and treating at least a portion of one or two conduits in a human or animal body, the therapeutic material can treat cancer. In an aspect, the therapeutic material that can treats cancer can comprise paclitaxel, cisplatin, platinum-taxane, carboplatin, cyclophosphamide, or docetaxel.

In an aspect of a method for diagnosing and treating at least a portion of one or two conduits in a human or animal body, the therapeutic material can treat ectopic pregnancy. In an aspect, the therapeutic material that can treat ectopic pregnancy can comprise methotrexate, PGF2a, or hypertonic glucose solution.

Disclosed herein is a method for treating cancer, comprising, (a) providing a delivery system that delivers an effective amount of a composition comprising an anti-cancer or chemotherapeutic material, wherein the delivery system comprises a delivery device comprising an introducer shaft comprising one or two exit ports for providing one or two catheters, one or two catheters each comprising an end structure on a delivery end, a composition comprising an anti-cancer or chemotherapeutic material, and a means for providing the composition comprising an anti-cancer or chemotherapeutic material into and through the one or two catheters; (b) delivering an effective amount of the composition comprising an anti-cancer or a chemotherapeutic material at or near a target site such that the anti-cancer or chemotherapeutic material contacts at least one fallopian tube, at least one ovary, the peritoneum, or a combination thereof.

In an aspect, the anti-cancer or chemotherapeutic material can comprise paclitaxel, cisplatin, platinum-taxane, carboplatin, cyclophosphamide, or docetaxel. In an aspect, the anti-cancer or chemotherapeutic material can comprise an anti-cancer or chemotherapeutic material known to the art.

In an aspect of a method for treating cancer, the introducer shaft can have one exit port and one catheter, and the composition comprising an anti-cancer or chemotherapeutic material can be provided into and through the one catheter. In an aspect of a method for treating cancer, the introducer shaft can have two exit ports and two catheters, and compositions comprising an anti-cancer or chemotherapeutic material can be provided into and through the two catheters.

In an aspect of a method for treating cancer, the disclosed method can comprise diagnosing at least a portion of a conduit prior to the delivering an effective amount of the composition comprising an anti-cancer or a chemotherapeutic material. In an aspect, one conduit can be diagnosed. In an aspect, two conduits can be diagnosed. In an aspect, diagnosing at least a portion of a conduit can comprise delivering an effective amount of the composition comprising a diagnostic material such that the material enters the lumen of the one or two conduits. In an aspect, the disclosed method can comprise treating at least a portion of one or two conduits. In an aspect, one conduit can be treated. In an aspect, two conduits can be treated. In an aspect, the method can comprise diagnosing at least one conduit following the treating of at least one conduit. In an aspect, one of the conduits can be a fallopian tube of a mammal. In an aspect, two of the conduits can be a fallopian tube of a mammal.

In an aspect of a method for treating cancer, each of the one or two catheters can have an attachment means on a proximal end. In an aspect, each of the one or two catheters can be a dual lumen balloon catheter. In an aspect, both catheters can be a dual lumen balloon catheter. In an aspect, the end structure of each of the one or two catheters can maintain the delivery end in an uterine cornua and can aid in localized delivery of a composition comprising an anti-cancer or chemotherapeutic material. In an aspect, the end structure of both catheters can maintain the delivery end in an uterine cornua and can aid in localized delivery of composition comprising an anti-cancer or chemotherapeutic material. In an aspect, the an anti-cancer or chemotherapeutic material can be embodied within a carrier, depot, injectable, capsule, particles, vessel, gels, fibers, or equivalent means for immediate, controlled, extended, or sustained delivery. In an aspect, the delivery can be immediate. In an aspect, the delivery can be controlled. In an aspect, the delivery can be extended. In an aspect, the delivery can be sustained.

Disclosed herein is a method for diagnosing at least a portion of one or two conduits in a human or animal body, comprising, (a) providing a delivery system that delivers an effective amount of a composition comprising a diagnostic material, wherein the delivery system comprises a delivery device comprising an introducer shaft comprising one or two exit ports for providing one or two catheters, one or two catheters each comprising an end structure on a delivery end, a composition comprising a diagnostic material, and a means for providing the composition comprising a diagnostic material into and through the one or two catheters; (b) delivering an effective amount of the composition comprising a diagnostic material such that the material enters at least a portion of the one or two conduits; and (c) diagnosing at least a portion of the one or two conduits with the composition comprising a diagnostic material. In an aspect, one conduit can be a fallopian tube of a mammal. In an aspect, both conduits can be a fallopian tube of a mammal. In an aspect of a disclosed method, one or more steps can be repeated. For example, in an aspect, a disclosed method can comprise repeating steps (b) and (c).

In an aspect of a method for diagnosing at least a portion of one or two conduits in a human or animal body, the introducer shaft can have one exit port and one catheter, and the composition comprising a diagnostic material can be provided into and through the one catheter. In an aspect of a method for diagnosing at least a portion of one or two conduits in a human or animal body, the introducer shaft can have two exit ports and two catheters, and the composition comprising a diagnostic material can be provided into and through the two catheters. In an aspect, each of the one or two catheters can have an attachment means on a proximal end. In an aspect, each of the one or two catheters can be a dual lumen balloon catheter. In an aspect, the end structure of each of the one or two catheters can maintain the delivery end in an uterine cornua and can aid in localized delivery of the composition comprising a diagnostic material.

In an aspect of a method for diagnosing at least a portion of one or two conduits in a human or animal body, diagnosing at least a portion of the one or two conduits with the composition can comprise a diagnostic material occurs without removal and re-introduction or substantial repositioning of the introducer shaft.

In an aspect of a method for diagnosing at least a portion of one or two conduits in a human or animal body, the composition can comprise a therapeutic material and the method can comprise treating at least a portion of the one or two conduits. In an aspect, one conduit can be treated. In an aspect, both conduits can be treated. In an aspect, treating at least a portion of the one or two conduits can comprise delivering an effective amount of a composition comprising a therapeutic material. In an aspect, steps (b) and (c) can be repeated after a treating step.

In an aspect, the therapeutic material can be embodied within a carrier, depot, injectable, capsule, particles, vessel, gels, fibers, or equivalent means for immediate, controlled, extended, or sustained delivery. In an aspect, the delivery can be immediate. In an aspect, the delivery can be controlled. In an aspect, the delivery can be extended. In an aspect, the delivery can be sustained.

In an aspect of a method for diagnosing and treating at least a portion of one or two conduits in a human or animal body, the therapeutic material can enhance fertility. In an aspect, the therapeutic material that can enhance fertility can comprise sperm material or ovulation inducing or stimulating hormones. In an aspect, the ovulation inducing or stimulating hormones can comprise one or more of Follistim, Gonal-F, Repronex, Menopur, Bravelle, Clomid, Serophene. In an aspect, a combination of ovulation inducing or stimulation hormones can be used to enhance fertility.

In an aspect of a method for diagnosing and treating at least a portion of one or two conduits in a human or animal body, the therapeutic material can treat cancer. In an aspect, the therapeutic material that can treats cancer can comprise paclitaxel, cisplatin, platinum-taxane, carboplatin, cyclophosphamide, or docetaxel.

In an aspect of a method for diagnosing and treating at least a portion of one or two conduits in a human or animal body, the therapeutic material can treat ectopic pregnancy. In an aspect, the therapeutic material that can treat ectopic pregnancy can comprise methotrexate, PGF2a, or hypertonic glucose solution.

Disclosed herein is a method for treating at least a portion of one or two conduits in a human or animal body, comprising, (a) providing a delivery system that delivers an effective amount of a composition comprising a therapeutic material, wherein the delivery system comprises a delivery device comprising an introducer shaft comprising one or two exit ports for providing one or two catheters, one or two catheters each comprising an end structure on a delivery end, a composition comprising a therapeutic material, and a means for providing the composition comprising a therapeutic material into and through the one or two catheters; (b) delivering an effective amount of the composition comprising a therapeutic material such that the material enters at least a portion of the one or two conduits and (c) treating at least a portion of the one or two conduits with the composition comprising a therapeutic material. In an aspect of a disclosed method, one or more steps can be repeated. For example, in an aspect, a disclosed method can comprise repeating steps (b) and (c). In an aspect, the one or two conduits can be a fallopian tube of a mammal.

In an aspect of a method for treating at least a portion of one or two conduits in a human or animal body, the introducer shaft can have one exit port and one catheter, and the composition comprising a therapeutic material can be provided into and through the one catheter. In an aspect of a method for diagnosing at least a portion of one or two conduits in a human or animal body, the introducer shaft can have two exit ports and two catheters, and the composition comprising a therapeutic material can be provided into and through the two catheters. In an aspect, each of the one or two catheters can have an attachment means on a proximal end. In an aspect, each of the one or two catheters can be a dual lumen balloon catheter. In an aspect, the end structure of each of the one or two catheters can maintain the delivery end in an uterine cornua and can aid in localized delivery of the composition comprising a therapeutic material.

In an aspect, the therapeutic material can be embodied within a carrier, depot, injectable, capsule, particles, vessel, gels, fibers, or equivalent means for immediate, controlled, extended, or sustained delivery. In an aspect, the delivery can be immediate. In an aspect, the delivery can be controlled. In an aspect, the delivery can be extended. In an aspect, the delivery can be sustained.

In an aspect of a method for treating at least a portion of one or two conduits in a human or animal body, the therapeutic material can enhance fertility. In an aspect, the therapeutic material that can enhance fertility can comprise sperm material or ovulation inducing or stimulating hormones. In an aspect, the ovulation inducing or stimulating hormones can comprise one or more of Follistim, Gonal-F, Repronex, Menopur, Bravelle, Clomid, Serophene. In an aspect, a combination of ovulation inducing or stimulation hormones can be used to enhance fertility.

In an aspect of a method for treating at least a portion of one or two conduits in a human or animal body, the therapeutic material can treat cancer. In an aspect, the therapeutic material that can treats cancer can comprise paclitaxel, cisplatin, platinum-taxane, carboplatin, cyclophosphamide, or docetaxel.

In an aspect of a method for treating at least a portion of one or two conduits in a human or animal body, the therapeutic material can treat ectopic pregnancy. In an aspect, the therapeutic material that treats ectopic pregnancy can comprise methotrexate, PGF2a, or hypertonic glucose solution.

In an aspect, a method for treating at least a portion of one or two conduits in a human or animal body can comprise diagnosing at least one conduit. In an aspect, diagnosing can occur prior to the delivering an effective amount of the composition comprising a therapeutic material such that the material enters at least a portion of the one or two conduits. In an aspect, diagnosis can occur following the treating at least a portion of the one or two conduits with the composition comprising a therapeutic material.

In an aspect, delivering an effective amount of a composition comprising therapeutic material can occur without removal and re-introduction or substantial repositioning of the introducer shaft.

In an aspect of a method for treating at least a portion of one or two conduits in a human or animal body, diagnosing at least a portion of one or two conduits can comprise delivering an effective amount of the composition comprising a diagnostic material such that the material enters the lumen of the one or two conduits.

Disclosed herein is a method for enhancing fertility, comprising, (a) providing a delivery system that delivers an effective amount of a composition comprising sperm material or ovulation inducing or stimulating hormones, wherein the delivery system comprises a delivery device comprising an introducer shaft comprising one or two exit ports for providing one or two catheters, one or two catheters each comprising an end structure on a delivery end, a composition comprising sperm material or ovulation inducing or stimulating hormones, and a means for providing the composition comprising sperm material or ovulation inducing or stimulating hormones into and through the one or two catheters; (b) delivering an effective amount of the composition comprising sperm material or ovulation inducing or stimulating hormones at or near a target site such that (i) the composition comprising the sperm material contacts at least one egg or oocyte in at least one fallopian tube to effect artificial insemination, or (ii) the composition comprising inducing or stimulating hormones contacts at least one ovary for induction or stimulation of ovulation. In an aspect, the target site can be a fallopian tube.

In an aspect, a method for enhancing fertility can comprise diagnosing at least one conduit. In an aspect, diagnosing can occur prior to delivering an effective amount of a composition comprising sperm material or ovulation inducing or stimulating hormones. In an aspect, diagnosing at least one conduit can comprise delivering an effective amount of the composition comprising a diagnostic material such that the material enters the lumen of the conduit. In an aspect, the at least one conduit is a fallopian tube of a mammal.

In an aspect of a disclosed method for enhancing fertility, the introducer shaft can have one exit port and one catheter, and the composition comprising the sperm material or ovulation inducing or stimulating hormones can be provided into and through the one catheter. In an aspect, the introducer shaft can have two exit ports and two catheters, and the composition comprising sperm material or ovulation inducing or stimulating hormones can be provided into and through the two catheters. In an aspect, the ovulation inducing or stimulating hormones comprise one or more of Follistim, Gonal-F, Repronex, Menopur, Bravelle, Clomid, Serophene, or a combination thereof.

In an aspect, the end structure of each of the one or two catheters can maintain the delivery end in an uterine cornua and can aid in localized delivery of the composition comprising sperm material or ovulation inducing or stimulating hormones. In an aspect, each of the one or two catheters can have an attachment means on a proximal end. In an aspect, each of the one or two catheters can be a dual lumen balloon catheter.

Disclosed herein is a method treating ectopic pregnancy, comprising, (a) providing a delivery system that delivers an effective amount of a composition comprising a therapeutic material, wherein the delivery system comprises a delivery device comprising an introducer shaft comprising one or two exit ports for providing one or two catheters, one or two catheters each comprising an end structure on a delivery end, a composition comprising a therapeutic material, and a means for providing the composition comprising a therapeutic material into and through the one or two catheters; (b) delivering an effective amount of the composition comprising a therapeutic material such that the therapeutic material contacts at least one fertilized egg. In an aspect, the therapeutic material can comprise methotrexate, PGF2a, or hypertonic glucose solution.

In an aspect of method for treating ectopic pregnancy, the introducer shaft can have one exit port and one catheter, and the composition comprising a therapeutic material can be provided into and through the one catheter. In an aspect, the introducer shaft can have two exit ports and two catheters, and the composition comprising a therapeutic material can be provided into and through the two catheters. In an aspect, the end structure of each of the one or two catheters can maintain the delivery end in an uterine cornua and can aid in localized delivery of the composition comprising a therapeutic material. In an aspect, each of the one or two catheters can be a dual lumen balloon catheter. In an aspect, each of the one or two catheters can have an attachment means on a proximal end.

In an aspect of method for treating ectopic pregnancy, the method can comprise diagnosing at least one conduit. In an aspect, diagnosing can occur prior to delivering an effective amount of the composition comprising a therapeutic material. In an aspect, diagnosing can occur after delivering an effective amount of the composition comprising a therapeutic material. In an aspect, diagnosing at least one conduit can comprise delivering an effective amount of the composition comprising a diagnostic material such that the material enters the lumen of the conduit. In an aspect, the at least one conduit can be a fallopian tube of a mammal.

Disclosed herein is a method for treatment of disease, comprising, (a) providing a delivery system that delivers an effective amount of a composition comprising a therapeutic material, wherein the delivery system comprises a delivery device comprising an introducer shaft comprising one or two exit ports for providing one or two catheters, one or two catheters each comprising an end structure on a delivery end, a composition comprising a therapeutic material, and a means for providing the composition comprising a therapeutic material into and through the one or two catheters; (b) delivering an effective amount of the composition comprising a therapeutic material at or near at least a portion of one or two conduits. In an aspect, the one or two conduits can be a fallopian tube of a mammal. In an aspect, the disease can be pelvic inflammatory disease. In an aspect, the therapeutic material can comprise doxycycline.

In an aspect, the therapeutic material can be embodied within a carrier, depot, injectable, capsule, particles, vessel, gels, fibers, or equivalent means for immediate, controlled, extended, or sustained delivery. In an aspect, the delivery can be immediate. In an aspect, the delivery can be controlled. In an aspect, the delivery can be extended. In an aspect, the delivery can be sustained.

In an aspect, the introducer shaft can have one exit port and one catheter, and the composition comprising a therapeutic material can be provided into and through the one catheter. In an aspect, the introducer shaft can have two exit ports and two catheters, and the composition comprising a therapeutic material can be provided into and through the two catheters.

In an aspect, each of the one or two catheters can have an attachment means on a proximal end. In an aspect, the end structure of each of the one or two catheters can maintain the delivery end in an uterine cornua and can aid in localized delivery of the composition comprising a therapeutic material. In an aspect, each of the one or two catheters can be a dual lumen balloon catheter.

In an aspect, a method for treating disease can comprise diagnosing at least a portion of one conduit. In an aspect, diagnosing can occur prior to delivering an effective amount of the composition comprising a therapeutic material. In an aspect, diagnosing can occur after delivering an effective amount of the composition comprising a therapeutic material. In an aspect, diagnosing at least one conduit can comprise delivering an effective amount of the composition comprising a diagnostic material such that the material enters the lumen of the conduit. In an aspect, the at least one conduit can be a fallopian tube of a mammal. In an aspect, diagnosing at least a portion of the one or conduit with the composition comprising a diagnostic material can occur without removal and re-introduction or substantial repositioning of the introducer shaft.

It is contemplated that the methods taught herein are effective with one application of material to at least one conduit, though the methods comprise at least one application to at least one conduit. Embodiments also comprise one or more applications of material to at least one conduit during one delivery cycle. For example, once the delivery device is in place in the uterus, with at least one end of the device at the site or sites to be evaluated, diagnostic material may be applied once, and then, without removal, one or more other applications of therapeutic material may be performed. Alternatively, therapeutic materials may be placed at the site or sites over multiple treatments. For each treatment, the delivery device would be inserted and removed. Such multiple applications may occur on consecutive days of insertion and removal or the days of insertion and removal may be interspersed with days of no applications of material. Such treatment regimens may be designed with individual patient needs taken into account by those skilled in the art, such as the treating physicians. Such treatment regimens may utilize the same or different compositions at each application.

In one method of delivery of the diagnostic or therapeutic material, pressure generated in the lumen of the delivery system forces the material through the delivery device, including at least one opening in at least one delivery end, out of the device and into the area. Once the material has been delivered, the delivery device is removed in whole or in part from the patient (the end structure may be detachable and fashioned from a resorbable material designed to be left in place). For example, once the material is delivered to the site, the delivery device can be collapsed, re-folded, re-sheathed, or directly removed in one or more pieces from the patient.

The compositions of the present invention comprise therapeutic materials and may further comprise one or more agents that are capable of providing other functions, including but not limited to, a curable carrier for the therapeutic material, allowing for controlled release of a substance, enhancing the ability of the therapeutic material to treat infertility, an ectopic pregnancy, infection, or cancer.

In general, the present invention comprises methods for diagnosing or treating at least one conduit in a human or animal body, comprising, providing a delivery system capable of delivering an effective amount of a composition comprising a diagnostic or therapeutic material, wherein the delivery system comprises a delivery device comprising at least an introducer shaft for providing at least one catheter; each catheter comprising an end structure on a delivery end and attachment means on a proximal end, a composition comprising a diagnostic or therapeutic material, and means for providing the composition into and through the catheters; delivering an effective amount of the composition at or near the target site such that the material allows for diagnosis or treatment of the lumen of the conduit. Means for providing the delivery composition include, but are not limited to, syringes and pressure systems, pumps, containers with plungers to force material into the catheters, or other methods and devices for moving flowable material through a catheter or tube. The methods may comprise diagnosing two conduits without removal and re-introduction or substantial repositioning of the introducer shaft. Such a method may be used to diagnose or treat fallopian tubes of a mammal.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention describe in detail methods, delivery systems, and compositions to diagnosis or treat the fallopian tubes of human, the present invention is not limited to these embodiments. There are numerous modifications or alterations that may suggest themselves to those skilled in the art for use of the methods, delivery systems, and compositions herein for the diagnosis or treatment of a variety of conduits in both human and non-human mammals.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Delivery of Representative Compositions Through Catheter

The catheter used in both device embodiments, shown in the Figures, were used to deliver composition standards at different viscosity levels to confirm acceptable delivery of the below representative list of diagnostic and therapeutic compounds.

| Compound Name | Use | Known Viscosity (cps) |
|---|---|---|
| Contrast (radiopaque) dye | Diagnostic | |
| Saline and air (sonographic contrast) | Diagnostic | |
| Sperm | Therapeutic | 9.35 +/− 0.99 |
| Methotrexate | Therapeutic | |
| Paclitaxel | Therapeutic | |
| Doxycycline | Therapeutic | |
| Fertilized egg | Therapeutic | |

REFERENCES

US Patent Documents

U.S. Pat. Nos. 3,405,711, 3,680,542, 3,803,308, 3,858,586, Re 29,345, Re 37,950, 4,136,695, 4,158,050, 4,160,446, 4,185,618, 4,245,623, 4,359,454, 4,509,504, 4,606,336, 4,664,112, 4,679,558, 4,681,106, 4,700,701, 4,700,705, 4,804,691, 4,824,434, 4,938,763, 4,983,177, 5,065,751, 5,095,917, 5,147,353, 5,278,201, 5,278,202, 5,324,519, 5,328,687, 5,340,849, 5,350,798, 5,469,867, 5,474,089, 5,487,897, 5,559,552, 5,612,052, 5,632,727, 5,681,873, 5,702,716, 5,714,159, 5,733,950, 5,736,152, 5,739,176, 5,744,153, 5,746,769, 5,747,058, 5,759,563, 5,780,044, 5,792,469, 5,826,584, 5,866,554, 5,888,533, 5,894,022, 5,935,137, 5,954,715, 5,962,006, 5,968,542, 5,979,446, 5,989,580, 5,990,194, 6,010,714, 6,019,757, 6,037,331, 6,042,590, 6,066,139, 6,068,626, 6,096,052, 6,112,747, 6,120,789, 6,130,200, 6,143,352, 6,145,505, 6,174,919, 6,176,240, 6,179,832, 6,297,337, 6,299,631, 6,306,243, 6,309,384, 6,327,505, 6,346,102, 6,357,443, 6,371,975, 6,395,293, 6,378,524, 6,401,719, 6,413,536, 6,413,539, 6,433,096, 6,455,064, 6,458,147, 6,461,631, 6,514,534, 6,514,535, 6,476,070, 6,485,486, 6,526,979, 6,528,080, 6,538,026, 6,565,557, 6,579,469, 6,599,299, 6,605,294, 6,605,667, 6,607,631, 6,620,846, 6,634,361, 6,663,607, 6,676,971, 6,679,266, 6,682,526, 6,684,884, 6,703,047, 6,723,144, 6,723,781, 6,743,248.

Foreign Patent Documents

WO 81/00701, WO 98/31308, WO 94/24944, WO 99/07297, WO 94/28803, WO 99/47073, WO 97/12569, WO 00/44323, WO 97/49345, WO 00/24374, WO 97/42987, WO 01/37760, WO 98/26737, WO 02/39880, WO 03/070085.

Other Publications

1. Toaff M, et al. Controlled ovarian hyperstimulation and transvaginal intratubal insemination as an alternative to gamete intrafallopian transfer. *Fertility and Sterility.* 1995; 64(4): 777-786.
2. Mamas L, et al. Comparison of fallopian tube sperm perfusion and intrauterine tuboperitoneal insemination: a prospective randomized study. *Fertility and Sterility.* 2006; 85(3): 735-740.
3. Confino E, et al. Selective salpingography for the diagnosis and treatment of early tubal pregnancy. *Fertility and Sterility.* 1994; 62(2): 286-288.
4. Armstrong K, et al. Intraperitoneal Cisplatin and Paclitaxel in Ovarian Cancer. *The New England Journal of Medicine.* 2006; 354(1): 34-43.
5. Cover N, et al. Synergetic effects of doxycycline-loaded chitosan nanoparticles for improving drug delivery and efficacy. *International Journal of Nanomedicine.* 2012; 7: 2411-2419.

What is claimed is:

1. A method of diagnosis and treatment, comprising,
   (a) providing one or more compositions to at least a portion of at least one fallopian tube of a human or animal by a delivery system that delivers an effective amount of the one or more compositions, wherein the one or more compositions comprises a first composition comprising at least one diagnostic material and a second composition comprising at least one therapeutic material, and wherein the delivery system comprises a delivery device comprising at least an introducer shaft comprising an atraumatic tip for positioning the tip at the uterine fundus and at least one exit port for providing at least one catheter; at least one catheter, wherein the at least one catheter comprises an end structure on a delivery end that maintains the delivery end in at least one uterine cornua and aids in localized delivery of the one or more compositions, and elements for providing the one or more compositions into and through the at least one catheter;
   (b) delivering an effective amount of the first composition such that the first composition enters at least a portion of the at least one fallopian tube; and
   (c) delivering an effective amount of the second composition such that the second composition enters at least a portion of the at least one fallopian tube.

2. The method of claim 1, wherein the first and second compositions are provided without removal and re-introduction or substantial repositioning of the introducer shaft.

3. The method of claim 1, wherein the first and second compositions are provided sequentially or simultaneously.

4. The method of claim 1, wherein the first and second compositions are the same composition.

5. The method of claim 1, wherein the first and second compositions are different compositions.

6. The method of claim 1, wherein the delivery system comprises an introducer shaft having one exit port and one catheter, and wherein the one or more compositions is provided into and through the one catheter.

7. The method of claim 1, wherein the delivery system comprises an introducer shaft having two exit ports and two catheters, and wherein the one or more compositions is provided into and through the two catheters.

8. The method of claim 1, wherein the at least one catheter is a dual lumen balloon catheter.

9. The method of claim 1, wherein the at least one catheter has an attachment means on a proximal end.

10. The method of claim 1, wherein the at least one therapeutic material is embodied within a carrier, depot, injectable, capsule, particles, vessel, gels, or fibers for delivery of the one or more compositions.

11. The method of claim 1, further comprising, (d) subjecting the human or animal to a visualization or imaging procedure.

12. The method of claim 11, further comprising, (e) diagnosing at least one fallopian tube following (d).

13. The method of claim 11, wherein the imaging procedure is ultrasound, fluoroscopy, magnetic resonance techniques, or combinations thereof.

14. The method of claim 1, wherein the at least one diagnostic material comprises materials that are fluid, fluid and gas, gas, semi-solids, gels, solids, and combinations thereof.

* * * * *